US011583683B2

(12) United States Patent
Perryman et al.

(10) Patent No.: US 11,583,683 B2
(45) Date of Patent: *Feb. 21, 2023

(54) WEARABLE ANTENNA ASSEMBLY

(71) Applicant: Stimwave Technologies Incorporated, Pompano Beach, FL (US)

(72) Inventors: Laura Tyler Perryman, Pompano Beach, FL (US); Elizabeth Greene, Pompano Beach, FL (US); Chad Andresen, Miami Beach, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/382,406

(22) Filed: Apr. 12, 2019

(65) Prior Publication Data
US 2020/0016416 A1 Jan. 16, 2020

Related U.S. Application Data

(63) Continuation of application No. 15/002,593, filed on Jan. 21, 2016, now Pat. No. 10,293,169, which is a (Continued)

(51) Int. Cl.
*A61N 1/372* (2006.01)
*H01Q 1/27* (2006.01)
(Continued)

(52) U.S. Cl.
CPC ......... *A61N 1/37229* (2013.01); *A61N 1/321* (2013.01); *A61N 1/37217* (2013.01);
(Continued)

(58) Field of Classification Search
CPC ................ A61N 1/321; A61N 1/37217; A61N 1/37229; A61N 1/3787; H01Q 1/273; H01Q 1/40
See application file for complete search history.

(56) References Cited

U.S. PATENT DOCUMENTS 2,990,547 A 6/1961 McDougal
3,662,758 A 5/1972 Glover
(Continued)

FOREIGN PATENT DOCUMENTS

CN 1678370 10/2005
CN 101185789 5/2008
(Continued)

OTHER PUBLICATIONS

US 5,197,469 A, 03/1993, Adams (withdrawn)
(Continued)

*Primary Examiner* — Christopher A Flory
(74) *Attorney, Agent, or Firm* — Fish & Richardson P.C.

(57) ABSTRACT

A wearable device for facilitating neurophysiological treatment of a patient harboring an implanted neural stimulator is provided. The wearable device includes a transmitting antenna configured to accept one or more input signals and to transmit one or more electromagnetic signals to a neural stimulator that is implanted in a patients body. The wearable device further includes a control circuitry configured to provide the one or more input signals to the transmitting antenna. The wearable device further includes a battery that provides electrical power to at least the control circuitry. The wearable device is configured to be worn outside the patient's body.

20 Claims, 30 Drawing Sheets

Related U.S. Application Data continuation of application No. 14/141,197, filed on Dec. 26, 2013, now Pat. No. 9,254,393.

(60) Provisional application No. 61/745,952, filed on Dec. 26, 2012.

(51) Int. Cl.
*A61N 1/32* (2006.01)
*H01Q 1/40* (2006.01)
*A61N 1/378* (2006.01)

(52) U.S. Cl.
CPC ............... *H01Q 1/273* (2013.01); *H01Q 1/40* (2013.01); *A61N 1/3787* (2013.01)

(56) References Cited

U.S. PATENT DOCUMENTS

| | | | |
|---|---|---|---|
| 3,663,758 A | 5/1972 | Erbert | |
| 3,727,616 A | 4/1973 | Lenzkes | |
| 4,057,069 A | 11/1977 | Dorffer et al. | |
| 4,102,344 A | 7/1978 | Conway et al. | |
| 4,223,679 A | 9/1980 | Schulman et al. | |
| 4,494,950 A | 1/1985 | Fischell | |
| 4,524,774 A | 6/1985 | Hildebrandt | |
| 4,525,774 A | 6/1985 | Kino et al. | |
| 4,532,930 A | 8/1985 | Crosby | |
| 4,561,443 A | 12/1985 | Hogrefe et al. | |
| 4,592,359 A | 6/1986 | Galbraith | |
| 4,612,934 A | 9/1986 | Borkan | |
| 4,628,933 A | 12/1986 | Michelson | |
| 4,665,896 A * | 5/1987 | LaForge | A61M 60/50 600/17 |
| 4,726,378 A * | 2/1988 | Kaplan | A61N 1/36036 607/115 |
| 4,736,747 A * | 4/1988 | Drake | A61N 1/37211 607/61 |
| 4,736,752 A | 4/1988 | Munck | |
| 4,741,339 A | 5/1988 | Harrison et al. | |
| 4,750,499 A | 6/1988 | Hoffer | |
| 4,793,353 A | 12/1988 | Borkan | |
| 4,837,049 A | 6/1989 | Byers et al. | |
| 4,926,879 A * | 5/1990 | Sevrain | A61F 11/04 340/407.1 |
| 4,947,844 A | 8/1990 | McDermott | |
| 5,058,581 A | 10/1991 | Silvian | |
| 5,070,535 A | 12/1991 | Hochmair et al. | |
| 5,193,539 A | 3/1993 | Schulman et al. | |
| 5,262,793 A | 11/1993 | Sperry | |
| 5,314,458 A | 5/1994 | Najafi et al. | |
| 5,343,766 A | 9/1994 | Lee | |
| 5,358,514 A | 10/1994 | Schulman et al. | |
| 5,411,535 A | 5/1995 | Fujii et al. | |
| 5,583,510 A | 12/1996 | Ponnapalli et al. | |
| 5,591,217 A | 1/1997 | Barreras | |
| 5,626,630 A | 5/1997 | Markowitz et al. | |
| 5,735,887 A | 4/1998 | Barreras, Sr. et al. | |
| 5,769,877 A | 6/1998 | Barreras | |
| 5,861,019 A | 1/1999 | Sun et al. | |
| 5,991,664 A | 11/1999 | Seligman | |
| 5,995,874 A | 11/1999 | Borza | |
| 6,141,588 A | 10/2000 | Cox et al. | |
| 6,164,284 A | 12/2000 | Shulman et al. | |
| 6,175,752 B1 | 1/2001 | Say et al. | |
| 6,350,335 B1 | 2/2002 | Hampel et al. | |
| 6,364,889 B1 | 4/2002 | Kheiri et al. | |
| 6,415,184 B1 | 7/2002 | Ishikawa et al. | |
| 6,445,953 B1 | 9/2002 | Bulkes et al. | |
| 6,445,955 B1 | 9/2002 | Michelson et al. | |
| 6,458,157 B1 | 10/2002 | Suaning | |
| 6,463,336 B1 | 10/2002 | Mawhinney | |
| D466,487 S | 12/2002 | Wada et al. | |
| 6,516,227 B1 | 2/2003 | Meadows et al. | |
| D474,982 S | 5/2003 | Wilson | |
| 6,564,807 B1 | 5/2003 | Schulman et al. | |
| 6,611,715 B1 | 8/2003 | Boveja | |
| 6,615,081 B1 | 9/2003 | Boveja | |
| 6,647,296 B2 | 11/2003 | Fischell et al. | |
| 6,662,052 B1 | 12/2003 | Sarwal et al. | |
| 6,684,104 B2 | 1/2004 | Gordon et al. | |
| 6,690,974 B2 | 2/2004 | Archer et al. | |
| 6,889,086 B2 | 5/2005 | Mass et al. | |
| 6,895,280 B2 | 5/2005 | Meadows et al. | |
| 6,972,727 B1 | 12/2005 | West et al. | |
| 7,003,350 B2 | 2/2006 | Denker et al. | |
| 7,027,874 B1 | 4/2006 | Sawan et al. | |
| 7,110,823 B2 | 9/2006 | Whitehurst et al. | |
| D529,402 S | 10/2006 | Burton | |
| 7,177,690 B2 | 2/2007 | Woods et al. | |
| 7,214,189 B2 | 5/2007 | Zdeblick | |
| 7,277,728 B1 | 10/2007 | Kauhanen | |
| 7,283,875 B2 | 10/2007 | Larsson | |
| 7,317,947 B2 | 1/2008 | Wahlstrand et al. | |
| 7,436,752 B2 | 10/2008 | He | |
| 7,450,992 B1 | 11/2008 | Cameron | |
| 7,471,257 B2 | 12/2008 | Candal et al. | |
| 7,489,248 B2 | 2/2009 | Gengel et al. | |
| 7,616,991 B2 | 11/2009 | Mann et al. | |
| 7,620,451 B2 | 11/2009 | Demarais | |
| 7,630,771 B2 | 12/2009 | Cauller | |
| 7,664,552 B2 | 2/2010 | Wahlstrand et al. | |
| D612,543 S | 3/2010 | Marseille | |
| 7,729,781 B2 | 6/2010 | Swoyer et al. | |
| 7,738,964 B2 | 6/2010 | Von Arx et al. | |
| 7,741,734 B2 | 6/2010 | Joannopoulos et al. | |
| 7,765,013 B2 | 7/2010 | Blick et al. | |
| 7,853,333 B2 | 12/2010 | Demarais | |
| 7,869,885 B2 | 1/2011 | Begnaud et al. | |
| 7,894,905 B2 | 2/2011 | Pless et al. | |
| 7,904,170 B2 | 3/2011 | Harding | |
| 7,908,014 B2 | 3/2011 | Schulman et al. | |
| 7,917,226 B2 | 3/2011 | Nghiem et al. | |
| 7,939,346 B2 | 5/2011 | Blick et al. | |
| D658,302 S | 4/2012 | Nixon | |
| 8,170,672 B2 | 5/2012 | Weiss et al. | |
| 8,242,968 B2 | 8/2012 | Comad et al. | |
| 8,320,850 B1 | 11/2012 | Khlat | |
| 8,332,040 B1 | 12/2012 | Winstrom | |
| 8,634,928 B1 | 1/2014 | O'Drisco et al. | |
| D701,504 S | 3/2014 | Christopher et al. | |
| D703,204 S | 4/2014 | Riddiford et al. | |
| D714,288 S | 9/2014 | Aumiller et al. | |
| 8,849,412 B2 | 9/2014 | Perryman et al. | |
| 8,903,502 B2 | 12/2014 | Perryman | |
| D721,701 S | 1/2015 | Al-Nasser | |
| D725,071 S | 3/2015 | Lee et al. | |
| D725,072 S | 3/2015 | Kim et al. | |
| D725,652 S | 3/2015 | Ishii | |
| D734,330 S | 7/2015 | Huang et al. | |
| 9,199,089 B2 | 12/2015 | Perryman et al. | |
| 9,220,897 B2 | 12/2015 | Perryman et al. | |
| 9,242,103 B2 | 1/2016 | Perryman et al. | |
| 9,254,393 B2 | 2/2016 | Perryman et al. | |
| 9,409,030 B2 | 8/2016 | Perryman et al. | |
| 9,566,449 B2 | 2/2017 | Perryman et al. | |
| 9,757,571 B2 | 9/2017 | Perryman | |
| 9,789,314 B2 | 10/2017 | Perryman | |
| 9,925,384 B2 | 3/2018 | Perryman et al. | |
| 9,974,965 B2 | 5/2018 | Andresen et al. | |
| 10,238,874 B2 | 3/2019 | Perryman | |
| 10,293,169 B2 | 5/2019 | Perryman et al. | |
| 10,315,039 B2 | 6/2019 | Perryman et al. | |
| 10,420,947 B2 | 9/2019 | Larson et al. | |
| 10,471,262 B2 | 11/2019 | Perryman et al. | |
| 10,953,228 B2 | 3/2021 | Perryman et al. | |
| 2001/0010662 A1 | 8/2001 | Saitou et al. | |
| 2002/0058972 A1 * | 5/2002 | Minogue | A61N 1/321 607/72 |
| 2002/0082668 A1 * | 6/2002 | Ingman | H02N 13/00 601/2 |
| 2002/0091420 A1 * | 7/2002 | Minogue | A61N 1/321 607/48 |
| 2002/0095195 A1 | 7/2002 | Mass | |

(56) References Cited

U.S. PATENT DOCUMENTS

| | | | |
|---|---|---|---|
| 2002/0103513 A1* | 8/2002 | Minogue | A61N 1/321 607/46 |
| 2002/0123779 A1 | 9/2002 | Arx et al. | |
| 2002/0128686 A1* | 9/2002 | Minogue | A61N 1/321 607/2 |
| 2002/0128693 A1* | 9/2002 | Minogue | A61N 1/321 607/40 |
| 2002/0133195 A1* | 9/2002 | Minogue | A61N 1/321 607/2 |
| 2003/0078633 A1 | 4/2003 | Firlik et al. | |
| 2003/0114898 A1 | 6/2003 | Von Arx et al. | |
| 2003/0114899 A1 | 6/2003 | Woods et al. | |
| 2003/0139782 A1 | 7/2003 | Duncan et al. | |
| 2003/0169207 A1* | 9/2003 | Beigel | H01Q 1/22 343/718 |
| 2003/0204224 A1 | 10/2003 | Torgerson et al. | |
| 2004/0044385 A1 | 3/2004 | Fenn et al. | |
| 2004/0059392 A1 | 3/2004 | Parramon et al. | |
| 2004/0082979 A1 | 4/2004 | Tong et al. | |
| 2004/0127942 A1 | 7/2004 | Yomtov et al. | |
| 2004/0138723 A1 | 7/2004 | Malick et al. | |
| 2004/0167587 A1* | 8/2004 | Thompson | A61N 1/37252 607/60 |
| 2004/0176803 A1 | 9/2004 | Whelan et al. | |
| 2004/0220621 A1 | 11/2004 | Zhou | |
| 2004/0230263 A1 | 11/2004 | Samulski | |
| 2004/0243208 A1 | 12/2004 | Jordan | |
| 2005/0027207 A1* | 2/2005 | Westbrook | A61B 5/7275 600/529 |
| 2005/0119716 A1 | 6/2005 | McClure et al. | |
| 2005/0137668 A1 | 6/2005 | Khan | |
| 2005/0245994 A1 | 11/2005 | Varrichio et al. | |
| 2006/0001583 A1 | 1/2006 | Bisig | |
| 2006/0003721 A1 | 1/2006 | Bisig | |
| 2006/0047327 A1* | 3/2006 | Colvin | H01Q 1/44 607/60 |
| 2006/0085039 A1 | 4/2006 | Hastings et al. | |
| 2006/0085042 A1 | 4/2006 | Hastings et al. | |
| 2006/0149331 A1 | 7/2006 | Man et al. | |
| 2006/0161216 A1 | 7/2006 | Constance | |
| 2006/0161225 A1* | 7/2006 | Sormann | A61N 1/3787 607/61 |
| 2006/0178718 A1 | 8/2006 | Jordan | |
| 2006/0206168 A1* | 9/2006 | Minogue | A61N 1/321 607/48 |
| 2006/0287686 A1 | 12/2006 | Cullen et al. | |
| 2006/0289528 A1 | 12/2006 | Chiu et al. | |
| 2007/0055322 A1 | 3/2007 | Forsberg et al. | |
| 2007/0055324 A1* | 3/2007 | Thompson | G16H 40/63 607/60 |
| 2007/0066995 A1 | 3/2007 | Strother et al. | |
| 2007/0100385 A1* | 5/2007 | Rawat | A61N 1/375 607/37 |
| 2007/0100395 A1 | 5/2007 | Ibrahim | |
| 2007/0100935 A1 | 5/2007 | Miyazaki et al. | |
| 2007/0106337 A1 | 5/2007 | Errico et al. | |
| 2007/0109208 A1 | 5/2007 | Turner | |
| 2007/0112402 A1 | 5/2007 | Grill et al. | |
| 2007/0123948 A1* | 5/2007 | Dal Molin | A41D 13/1281 607/32 |
| 2007/0156179 A1 | 7/2007 | S.E. | |
| 2007/0208394 A1 | 9/2007 | King et al. | |
| 2007/0213773 A1 | 9/2007 | Hill et al. | |
| 2007/0213783 A1 | 9/2007 | Pless | |
| 2007/0239224 A1 | 10/2007 | Bennett et al. | |
| 2007/0254632 A1 | 11/2007 | Beadle et al. | |
| 2007/0255223 A1* | 11/2007 | Phillips | A61N 1/3787 604/179 |
| 2007/0255373 A1 | 11/2007 | Metzler et al. | |
| 2007/0257636 A1* | 11/2007 | Phillips | A61N 1/3787 320/108 |
| 2007/0265543 A1 | 11/2007 | VanSickle et al. | |
| 2007/0265690 A1 | 11/2007 | Lichtenstein et al. | |
| 2007/0288066 A1 | 12/2007 | Christman et al. | |
| 2007/0293909 A1 | 12/2007 | Cowan et al. | |
| 2008/0010358 A1 | 1/2008 | Jin | |
| 2008/0046012 A1 | 2/2008 | Covalin et al. | |
| 2008/0077184 A1 | 3/2008 | Denker et al. | |
| 2008/0077188 A1 | 3/2008 | Denker et al. | |
| 2008/0077189 A1 | 3/2008 | Ostroff | |
| 2008/0103558 A1 | 5/2008 | Wenzel | |
| 2008/0154217 A1 | 6/2008 | Carrez et al. | |
| 2008/0161883 A1* | 7/2008 | Conor | A61N 1/0456 607/48 |
| 2008/0266123 A1 | 10/2008 | Ales et al. | |
| 2008/0279896 A1* | 11/2008 | Heinen | A61P 9/00 424/239.1 |
| 2008/0281244 A1 | 11/2008 | Jacobs | |
| 2009/0018599 A1 | 1/2009 | Hastings et al. | |
| 2009/0099405 A1 | 4/2009 | Schneider et al. | |
| 2009/0105784 A1 | 4/2009 | Massoud-Ansari | |
| 2009/0105795 A1* | 4/2009 | Minogue | A61N 1/36003 607/148 |
| 2009/0125091 A1 | 5/2009 | Schoenbach et al. | |
| 2009/0132002 A1 | 5/2009 | Kieval | |
| 2009/0132003 A1 | 5/2009 | Borgens et al. | |
| 2009/0200985 A1 | 8/2009 | Zane et al. | |
| 2009/0204170 A1 | 8/2009 | Hastings et al. | |
| 2009/0234407 A1 | 9/2009 | Hastings et al. | |
| 2009/0248112 A1 | 10/2009 | Mumbru et al. | |
| 2009/0251101 A1* | 10/2009 | Phillips | A61M 5/14276 320/108 |
| 2009/0270948 A1 | 10/2009 | Nghiem et al. | |
| 2009/0270951 A1* | 10/2009 | Kallmyer | A61N 1/3787 607/61 |
| 2009/0292339 A1 | 11/2009 | Erickson | |
| 2010/0010565 A1 | 1/2010 | Lichtenstein et al. | |
| 2010/0053789 A1 | 3/2010 | Duric et al. | |
| 2010/0114143 A1* | 5/2010 | Albrecht | A41D 13/1281 606/191 |
| 2010/0114198 A1 | 5/2010 | Donofrio et al. | |
| 2010/0125269 A1 | 5/2010 | Emmons et al. | |
| 2010/0125312 A1* | 5/2010 | Stevenson | A61N 1/36135 607/45 |
| 2010/0137938 A1 | 6/2010 | Kishawi et al. | |
| 2010/0168818 A1* | 7/2010 | Barror | A61N 1/37512 607/60 |
| 2010/0174340 A1 | 7/2010 | Simon | |
| 2010/0179449 A1 | 7/2010 | Chow et al. | |
| 2010/0198039 A1 | 8/2010 | Towe | |
| 2010/0198307 A1* | 8/2010 | Toy | A61N 1/37235 607/60 |
| 2010/0231382 A1 | 9/2010 | Tayrani et al. | |
| 2010/0234919 A1* | 9/2010 | Minogue | A61N 1/321 607/48 |
| 2010/0234922 A1 | 9/2010 | Forsell | |
| 2010/0241051 A1 | 9/2010 | Dacey, Jr. et al. | |
| 2010/0268298 A1 | 10/2010 | Moffitt et al. | |
| 2010/0269339 A1 | 10/2010 | Dye et al. | |
| 2010/0298742 A1 | 11/2010 | Perlman et al. | |
| 2010/0331934 A1 | 12/2010 | McDonald et al. | |
| 2011/0029043 A1 | 2/2011 | Frysz et al. | |
| 2011/0040350 A1 | 2/2011 | Griffith | |
| 2011/0054563 A1 | 3/2011 | Janzig et al. | |
| 2011/0074342 A1 | 3/2011 | MacLaughlin | |
| 2011/0077698 A1 | 3/2011 | Tsampazis et al. | |
| 2011/0098583 A1 | 4/2011 | Pandia et al. | |
| 2011/0106220 A1 | 5/2011 | DeGiorgio et al. | |
| 2011/0120822 A1 | 5/2011 | Kondou et al. | |
| 2011/0121822 A1 | 5/2011 | Parsche | |
| 2011/0125214 A1 | 5/2011 | Goetz et al. | |
| 2011/0130804 A1 | 6/2011 | Lin et al. | |
| 2011/0144468 A1 | 6/2011 | Boggs et al. | |
| 2011/0152750 A1 | 6/2011 | Dacey, Jr. et al. | |
| 2011/0166630 A1* | 7/2011 | Phillips | A61N 1/3787 607/61 |
| 2011/0172733 A1* | 7/2011 | Lima | A61N 1/37223 607/42 |
| 2011/0190849 A1 | 8/2011 | Faltys et al. | |
| 2011/0208266 A1* | 8/2011 | Minogue | A61B 5/296 607/49 |

(56) References Cited

U.S. PATENT DOCUMENTS

| | | | |
|---|---|---|---|
| 2011/0245892 A1* | 10/2011 | Kast | A61N 1/3787 607/65 |
| 2011/0276108 A1* | 11/2011 | Crowe | A61N 1/36007 607/48 |
| 2012/0004708 A1 | 1/2012 | Chen et al. | |
| 2012/0004709 A1 | 1/2012 | Chen et al. | |
| 2012/0116477 A1* | 5/2012 | Crowe | A61N 1/321 607/46 |
| 2012/0143282 A1 | 6/2012 | Fukui et al. | |
| 2012/0158407 A1* | 6/2012 | Forsell | A61N 1/37217 704/275 |
| 2012/0194399 A1 | 8/2012 | Bily et al. | |
| 2012/0215218 A1 | 8/2012 | Lipani | |
| 2012/0239107 A1* | 9/2012 | Kallmyer | A61N 1/3787 607/41 |
| 2012/0283800 A1* | 11/2012 | Perryman | A61N 1/3727 607/60 |
| 2012/0302821 A1* | 11/2012 | Burnett | A61N 2/008 600/14 |
| 2012/0330384 A1 | 12/2012 | Perryman et al. | |
| 2013/0016016 A1 | 1/2013 | Lin et al. | |
| 2013/0066400 A1 | 3/2013 | Perryman et al. | |
| 2013/0079849 A1 | 3/2013 | Perryman et al. | |
| 2013/0131752 A1* | 5/2013 | Rawat | A61N 1/37518 607/32 |
| 2013/0018439 A1 | 6/2013 | Chow et al. | |
| 2013/0165991 A1 | 6/2013 | Kim | |
| 2013/0226262 A1* | 8/2013 | Stevenson | A61N 1/36135 607/45 |
| 2013/0310901 A1* | 11/2013 | Perryman | A61N 1/37229 607/72 |
| 2014/0031837 A1 | 1/2014 | Perryman et al. | |
| 2014/0047713 A1 | 2/2014 | Singh et al. | |
| 2014/0058480 A1 | 2/2014 | Perryman et al. | |
| 2014/0058481 A1 | 2/2014 | Perryman et al. | |
| 2014/0169142 A1 | 6/2014 | Heck et al. | |
| 2014/0266935 A1 | 9/2014 | Tankiewicz | |
| 2014/0336727 A1 | 11/2014 | Perryman et al. | |
| 2015/0182753 A1 | 7/2015 | Harris et al. | |
| 2015/0321017 A1 | 11/2015 | Perryman et al. | |
| 2016/0101287 A1 | 4/2016 | Perryman | |
| 2016/0136439 A1 | 5/2016 | Andresen et al. | |
| 2016/0339258 A1 | 11/2016 | Perryman et al. | |
| 2016/0361535 A1 | 12/2016 | Perryman et al. | |
| 2016/0367825 A1 | 12/2016 | Perryman et al. | |
| 2017/0036033 A9 | 2/2017 | Perryman et al. | |
| 2018/0008828 A1 | 1/2018 | Perryman | |
| 2018/0169423 A1 | 6/2018 | Larson et al. | |
| 2018/0236248 A1 | 8/2018 | Perryman | |
| 2018/0264277 A1 | 9/2018 | Perryman | |
| 2019/0229771 A1 | 7/2019 | Lee et al. | |
| 2019/0247660 A1 | 8/2019 | Perryman | |
| 2019/0381327 A1 | 12/2019 | Perryman et al. | |
| 2020/0016415 A1 | 1/2020 | Perryman et al. | |
| 2020/0222703 A1 | 7/2020 | Perryman et al. | |
| 2021/0187311 A1 | 6/2021 | Perryman et al. | |
| 2021/0275813 A1 | 9/2021 | Perryman et al. | |
| 2022/0088398 A1 | 3/2022 | Perryman et al. | |
| 2022/0126105 A1 | 4/2022 | Perryman et al. | |

FOREIGN PATENT DOCUMENTS

| | | |
|---|---|---|
| CN | 101217320 | 7/2008 |
| CN | 101352596 | 1/2009 |
| CN | 101773701 | 7/2010 |
| CN | 101842131 | 9/2010 |
| CN | 201676401 | 12/2010 |
| CN | 102120060 | 7/2011 |
| EP | 2462981 | 6/2001 |
| EP | 1588609 | 10/2005 |
| EP | 2694154 | 1/2018 |
| EP | 3403690 | 8/2020 |
| ES | 2341347 | 6/2010 |
| JP | H10 509901 | 9/1998 |
| JP | 2002524124 | 8/2002 |
| JP | 2005531371 | 10/2005 |
| JP | 200823353 | 2/2008 |
| JP | 2008161667 | 7/2008 |
| JP | 2008528222 | 7/2008 |
| JP | 2009523402 | 6/2009 |
| JP | 2010534114 | 11/2010 |
| JP | 201155912 | 3/2011 |
| JP | 2011510787 | 4/2011 |
| JP | 2012508624 | 4/2012 |
| WO | WO9620754 | 7/1996 |
| WO | WO 200013585 | 3/2000 |
| WO | WO2004002572 | 1/2004 |
| WO | WO 2004004826 | 1/2004 |
| WO | WO 2006113 802 | 10/2006 |
| WO | WO 2006/128037 | 11/2006 |
| WO | WO 2007059386 | 5/2007 |
| WO | WO 2007081971 | 7/2007 |
| WO | WO2009015005 | 1/2009 |
| WO | WO 2010/005746 | 1/2010 |
| WO | WO 2010051189 | 5/2010 |
| WO | WO 2010053789 | 5/2010 |
| WO | WO 2010057046 | 5/2010 |
| WO | WO 2010104569 | 9/2010 |
| WO | WO 2011079309 | 6/2011 |
| WO | WO 2012103519 | 8/2012 |
| WO | WO 2012138782 | 10/2012 |
| WO | WO 2013019757 | 2/2013 |
| WO | WO 2013025632 | 2/2013 |
| WO | WO 2013040549 | 3/2013 |

OTHER PUBLICATIONS

U.S. Appl. No. 14/445,159, filed Nov. 13, 2014, Perryman et al.
U.S. Appl. No. 29/478,687, filed Jan. 7, 2003, Perryman et al.
Communication from the European Patent Office in EP Appln. No. 12767575.9, dated Nov. 7, 2014, 7 pages.
EP European Search Report in European Appln. No. 17208566.4, dated Sep. 26, 2018, 14 pages.
EP Extended European Search Report in European Appln. No. 18150779.9, dated May 9, 2018, 7 pages.
EP Office Action in European Appln, No. 12740011.7, dated Sep. 18, 2018, 21 pages.
EP Office Action in European Appln, No. 15793285.6, dated Oct. 4, 2018, 6 pages.
EP Partial Supplementary European Search Report in European Appln. No. 12831083.6, dated Mar. 24, 2015, 7 pages.
European Search Report in European Appln. No. 12767575.9, dated Jan. 11, 2018, 6 pages.
European Search Report in European Appln. No. EP19186209, dated Nov. 25, 2019, 9 pages.
Examination Report in Appln. No. 2012240239, dated May 9, 2016, 3 pages.
Examination Report in Appln. No. 2012308197, dated Apr. 22, 2016, 5 pages.
Extended European Search report in Appln. No. 12740011.7, dated Sep. 9, 2015, 6 pages.
Extended European Search report in Appln. No. 12767575.9, dated Nov. 7, 2014, 7 pages.
Extended European Search Report in Appln. No. 1281083.6, dated Aug. 17, 2015, 9 pages.
Extended European Search report in Appln. No. 12819482.6, dated Apr. 28, 2015, 7 pages.
Extended European Search Report in Appln. No. 12824347.4, dated Apr. 22, 2015, 6 pages.
Extended European Search Report in Appln. No. 12824347.4, dated May 11, 2015, 1 page.
Extended European Search Report in Appln. No. 15793285.6, dated Dec. 12, 2017, 7 pages.
Iannetta [online], "Nov. 2014 New Products: Wearable coil facilities positioning during prostate MRI," Urology Times, retrieved on Nov. 10, 2014, retrieved from<URL: http://urologytimes.modernmedicine.com/urology-times/news/november-2014-new-products-wearable-coil-facilitates-positioning-during-prostate-mri?page=full>, 7 pages.

(56) References Cited

OTHER PUBLICATIONS

O'Driscoll et al., "A mm-Sized implantable power receiver with adaptive link compensation," Poster, Presented at IEEE International Soild-State Corcuits Conference, Session 17, 2009, 3 pages.
PCT International Preliminary Report on Patentability and Written Opinion in International Appln. No. PCT/US2012/023029, dated Jan. 28, 2014, 9 pages.
PCT International Preliminary Report on Patentability and Written Opinion in International Appln. No. PCT/US2012/032200 dated Oct. 8, 2013, 11 pages.
PCT International Preliminary Report on Patentability and Written Opinion in International Appln. No. PCT/US2012/048903, dated Mar. 25, 2014, 8 pages.
PCT International Preliminary Report on Patentability in International Appln. No. PCT/US2013/077846, dated Jun. 30, 2015, 6 pages.
PCT International Preliminary Report on Patentability issued in International Appl. No. PCT/US2012/055746, dated Mar. 18, 2014, 10 pages.
PCT International Preliminary Report on Patentability issued in International Appln. No. PCT/US2012/050633, dated Feb. 18, 2014, 7 pages.
PCT International Search Report and PCT Written Opinion of the International Searching Authority in International Appln. No. PCT/US2012/055746, dated Jan. 3, 2013, 11 pages.
PCT International Search Report and the Written Opinion in Appln. No. PCT/US2012/048903 dated Oct. 10, 2012, 10 pages.
PCT International Search Report and Written Opinion in International Appln. No. PCT/US2012/050633 dated Oct. 23, 2012, 8 pages.
PCT International Search Report and Written Opinion in International Appln. No. PCT/US2012/023029, dated May 16, 2012, 11 pages.
PCT International Search Report and Written Opinion in International Appln. No. PCT/US2012/032200, datedJul. 27, 2012, 11 pages.
PCT International Search Report and Written Opinion in International Appln. No. PCT/US2013/077846 dated Apr. 21, 2014, 10 pages.
PCT International Search Report and Written Opinion in International Appln. No. PCT/US2015/030433, dated Sep. 29, 2015, 14 pages.
pharad.com [online], "Assembly, Wearable Antenna, 350-450 MHz,"retrieved on Oct. 14, 2010, retrieved from URL< http://www.pharad.com/pdf/UHF-Wearable-Antenna-2D.pdf>, 1 page.
Poon et al., "Optimal frequency for wireless power transmission into dispersive tissue," IEEE Transactions on Antennas and Propagation, May 2010, 58(5):1739-1750.
wirelessdesignmag.com [online], "Pharad at Forefront of LTE Antenna Innovation with Develpoment of LTE Wearable Antenna," retrieved on Aug. 12, 2012, retrieved from<URL:http://www.wirelessdesignmag.com/product-release/2013/08/pharad-forefront-lte-antenna-innovation-development-lte-wearable-antenna>, 3 pages.
CA Office Action in Canadian Appln. No. 2831138, dated Oct. 30, 2020, 4 pages.
IL Office Action in Israeli Appln. No. 256280.0, dated Sep. 16, 2020, 9 pages (with English Translation).
CN OA in Chinese Appln. No. 201710675346.5, dated Jun. 1, 2020, 11 pages (with English translation).
PCT International Search Report and Written Opinion in International Appln. No. PCT/US2020/013155, dated Apr. 1, 2020, 8 pages.
EP Extended European Search Report in European Appln. No. 20209052.8, dated Apr. 14, 2021, 7 pages.
International Preliminary Report on Patentability in International Appln. No. PCT/US2020/013155, dated Jul. 22, 2021, 8 pages.
Extended European Search Report in Emopean Appln. No. 21164580.9, dated Oct. 22, 2021, 8 pages.
Extended European Search Report in European Appln No. 20738285.4, dated Aug. 17, 2022, 5 pages.

* cited by examiner

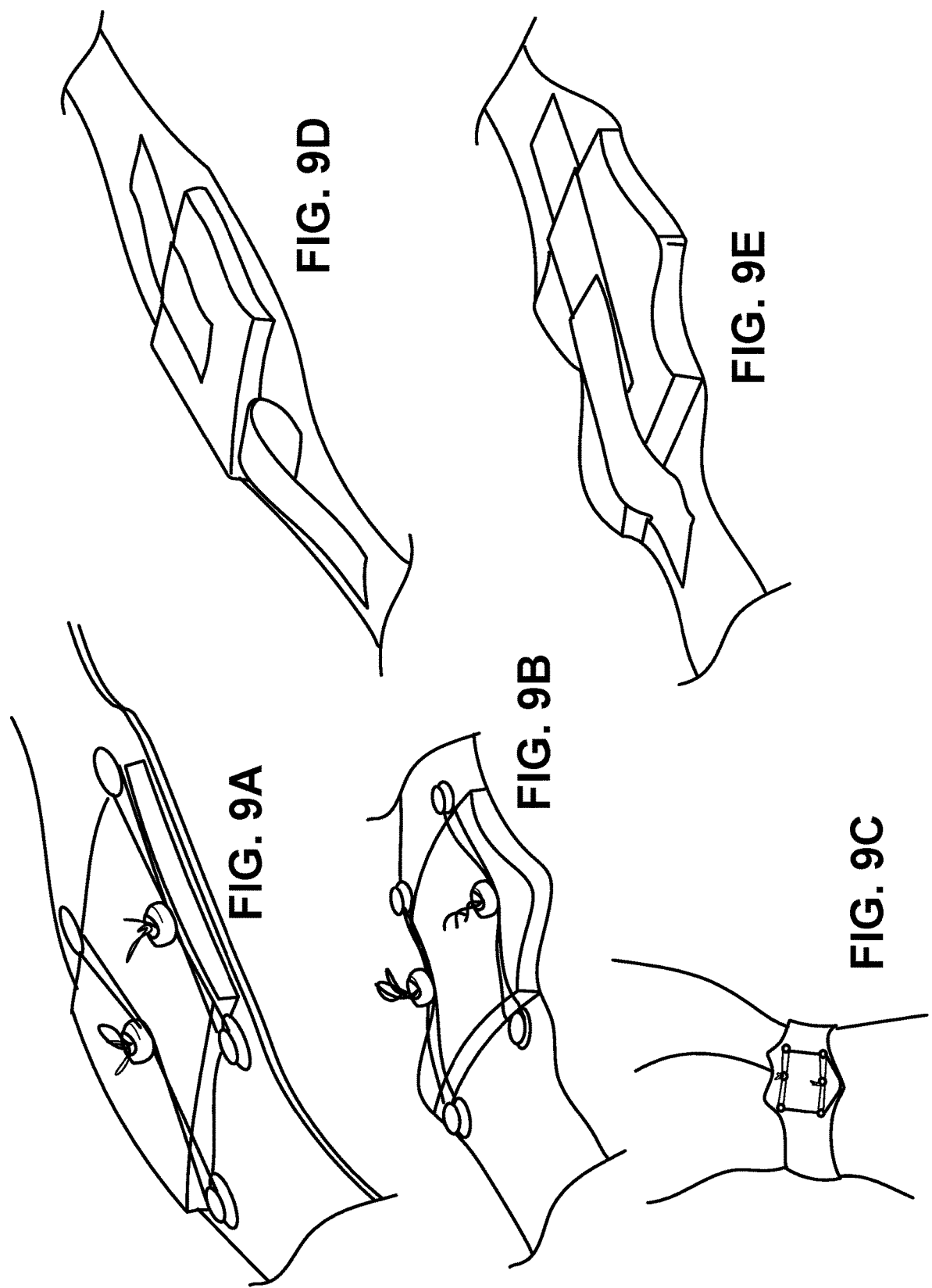

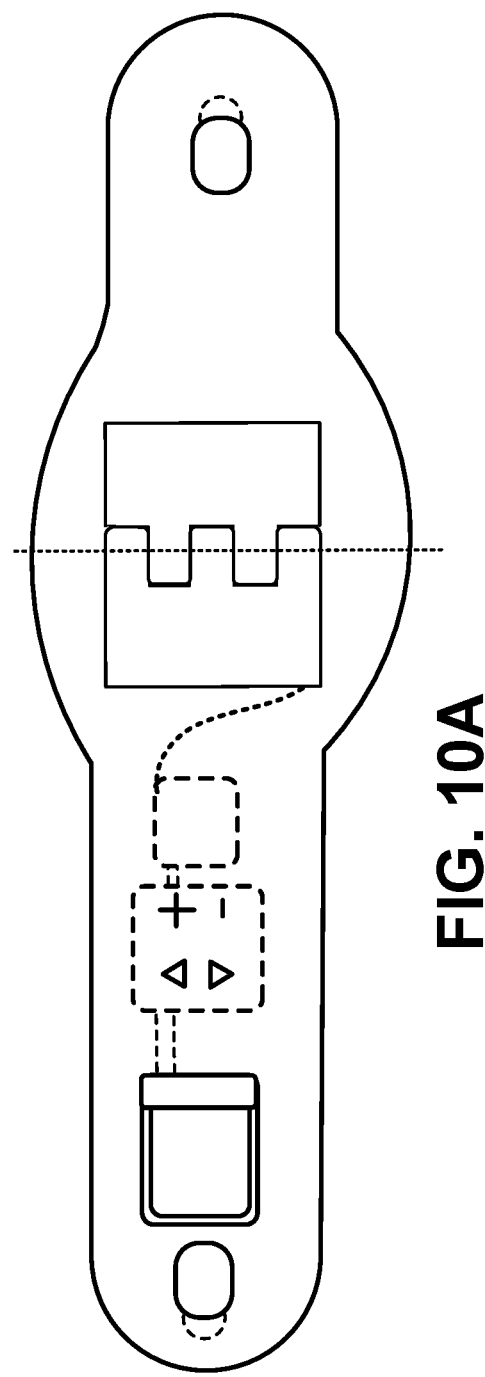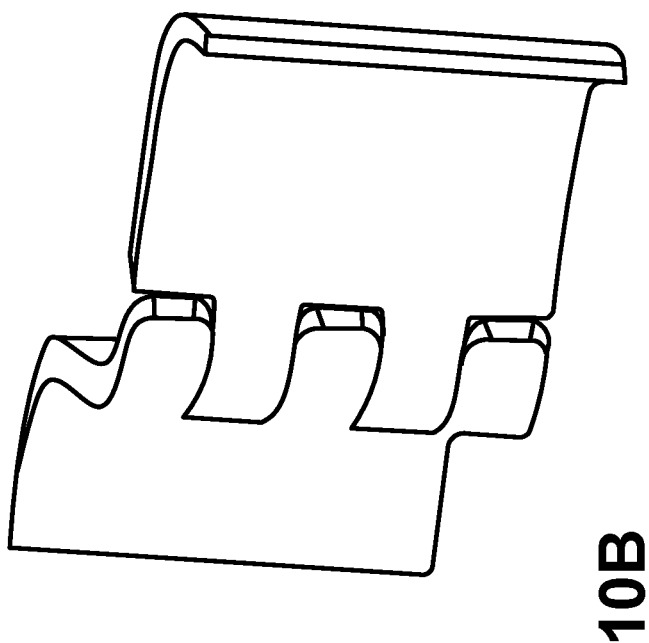
FIG. 10A
FIG. 10B

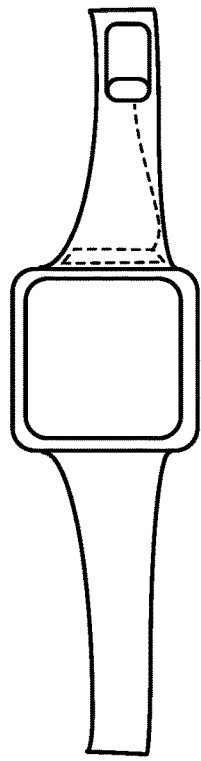
FIG. 29
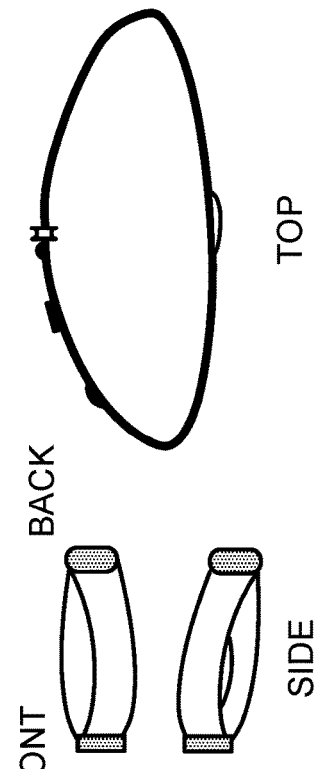
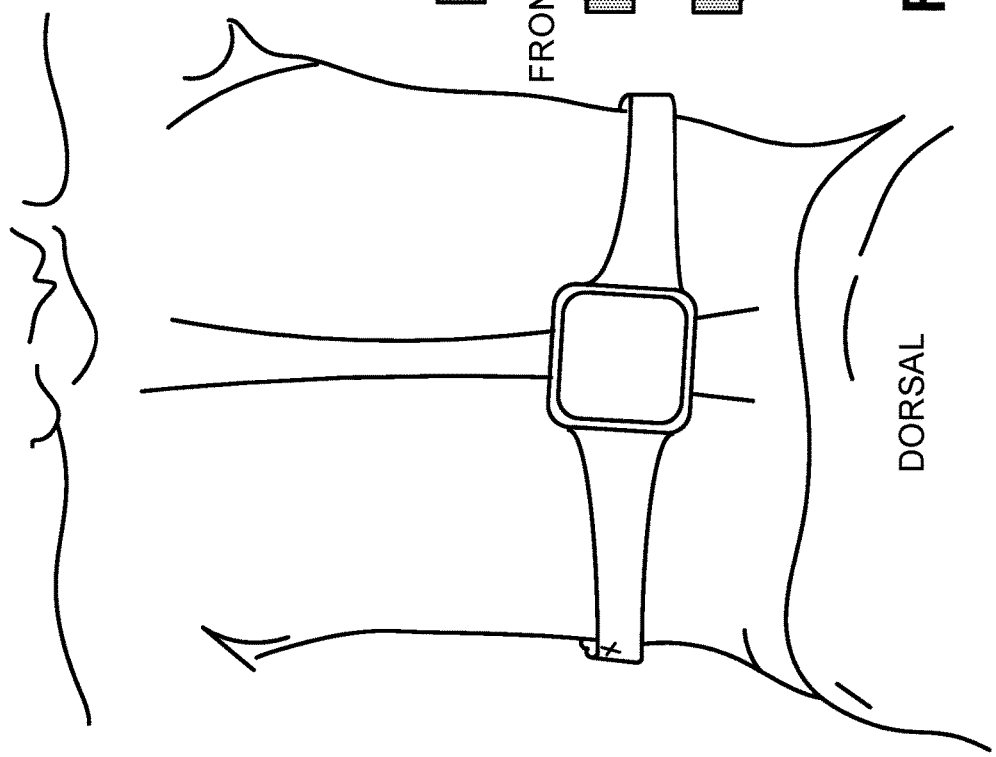
FIG. 30

WEARABLE ANTENNA ASSEMBLY

CROSS-REFERENCE TO RELATED APPLICATIONS

This application is a continuation of U.S. application Ser. No. 15/002,593, filed Jan. 21, 2016, now allowed, which is a continuation of U.S. application Ser. No. 14/141,197, filed Dec. 26, 2013, now U.S. Pat. No. 9,254,393, issued Feb. 9, 2016, which claims the benefit of U.S. Provisional Patent Application No. 61/745,952, filed Dec. 26, 2012. The contents of all of these applications are incorporated by reference in their entirety.

BACKGROUND

Neural modulation of neural tissue in the body by electrical stimulation has become an important type of therapy for chronic disabling conditions, such as chronic pain, problems of movement initiation and control, involuntary movements, dystonia, urinary and fecal incontinence, sexual difficulties, vascular insufficiency, heart arrhythmia, and more. Electrical stimulation of the spinal column and nerve bundles leaving the spinal cord was the first approved neural modulation therapy and has been used commercially since the 1970s. Implanted electrodes are used to pass pulsatile electrical currents of controllable frequency, pulse width, and amplitudes. Two or more electrodes are in contact with neural elements, chiefly axons, and can selectively activate varying diameters of axons, with positive therapeutic benefits. A variety of therapeutic intra-body electrical stimulation techniques are utilized to treat neuropathic conditions that utilize an implanted neural stimulator in the spinal column or surrounding areas, including the dorsal horn, dorsal root ganglia, dorsal roots, dorsal column fibers, and peripheral nerve bundles leaving the dorsal column or brain, such as vagus-, occipital-, trigeminal-, hypoglossal-, sacral-, and coccygeal nerves.

SUMMARY OF THE INVENTION

A wearable device for facilitating neurophysiological treatment of a patient harboring an implanted neural stimulator is provided. The wearable device includes a transmitting antenna configured to accept one or more input signals and to transmit one or more electromagnetic signals to a neural stimulator that is implanted in a patient's body. The wearable device further includes a control circuitry configured to provide the one or more input signals to the transmitting antenna. The wearable device further includes a battery that provides electrical power to at least the control circuitry. The wearable device is configured to be worn outside the patient's body.

In some embodiments the control circuitry includes a microwave field stimulator.

In some embodiments, the transmitting antenna is a patch antenna.

In some embodiments, the wearable device further includes an inductive charging component for transferring electrical energy to the battery.

In some embodiments, the wearable device further includes a control panel with at least one interface button.

In some embodiments, a first interface button of the at least one interface button controls at least one neurostimulation setting of the control circuitry.

In some embodiments, the at least one neurostimulation setting includes at least one of an amplitude setting, a pulse width setting, a frequency setting, and a preset programs setting.

In some embodiments, a second interface button of the at least one interface button controls which neurostimulation setting of the at least one neurostimulation setting is controlled by the first interface button.

In some embodiments, the wearable device includes a belt member, and the transmitting antenna, control circuitry and battery are mounted on the belt member.

In some embodiments, the belt member has a length-wise dimension (a circumference) sized to allow the patient to wear the wearable device about a torso portion of the patient's body.

In some embodiments, the belt member includes at least one flexible portion and at least one rigid portion.

In some embodiments, the transmitting antenna is mounted on a rigid portion of the belt member and the control circuitry is mounted on a rigid portion of the belt member.

In some embodiments, the circumference is adjustable by the patient.

In some embodiments, a portion of the wearable device includes a plurality of layers substantially parallel to a surface of the patient's body, the plurality of layers includes: a ground plane; a conductor layer between the ground plane and the surface of the patient's body; and a dielectric layer between the conductor layer and the surface of the patient's body.

In some embodiments, the plurality of layers further includes: a first layer of foam between the ground plane and the conductor layer; and a second layer of foam between the conductor layer and the dielectric layer.

In some embodiments, the transmitting antenna is tuned with the dielectric layer to match a coupling of the surface of the patient's body so that a dielectric fluid is not necessary between the dielectric layer and the surface of the patient's body.

In some embodiments, the battery is removable from the wearable device to allow for battery replacement.

In some embodiments, the battery is rechargeable.

BRIEF DESCRIPTION OF THE DRAWINGS

FIG. 3A shows the top view of a structural option for a wearable antenna assembly. FIG. 3B shows the profile view a structural option for a wearable antenna assembly.

FIGS. 9A-E demonstrates tensioners used to hold the shape of a flexible transmitting antenna embedded within the wearable antenna assembly to maintain the concave curvature of the individual patient's waist.

FIG. 9A illustrates a flexible transmitting antenna embedded within the wearable antenna assembly while the pull-string tensioners are not engaged and the antenna is flat.

FIG. 9B illustrates a flexible transmitting antenna embedded within the wearable antenna assembly while the pull-string tensioners are engaged and the antenna's flexible shape is maintained.

FIG. 9C illustrates a wearable antenna assembly on a patient where the pull-string tensioners are engaged and the embedded antenna's flexible shape conforms to the lumbar crevice of the patient.

FIG. 9D illustrates an embedded antenna while the Velcro straps are not engaged and the embedded antenna's flexible shape is not maintained.

FIG. 9E illustrates an embedded antenna while the Velcro straps are engaged and the embedded antenna's flexible shape is maintained.

FIG. 10A illustrates a wearable antenna assembly with a two-piece antenna with interlocking fingers that give greater conformity to the lumbar crevice.

FIG. 10B illustrates a two-piece antenna with interlocking fingers that adjust along the caudal-cranial axis.

FIG. 18A illustrates the process of depositing materials to create the antenna stack up. FIG. 18B is a block diagram depicting the antenna layers for an assembly where the dielectric, conducting planes, and foam are deposited in to create an ultra-thin profile.

FIG. 29 is an example of a placement of the microwave field stimulator on the wearable antenna assembly.

FIG. 30 illustrates the use of differential positioning sensors placed on the wearable antenna to alert the user and adjust stimulation.

DETAILED DESCRIPTION

The following detailed description explains various embodiments of the invention. These embodiments are merely illustrative, and those of skill in the art will recognize that other embodiments fall within the scope of the invention.

Figure 1:
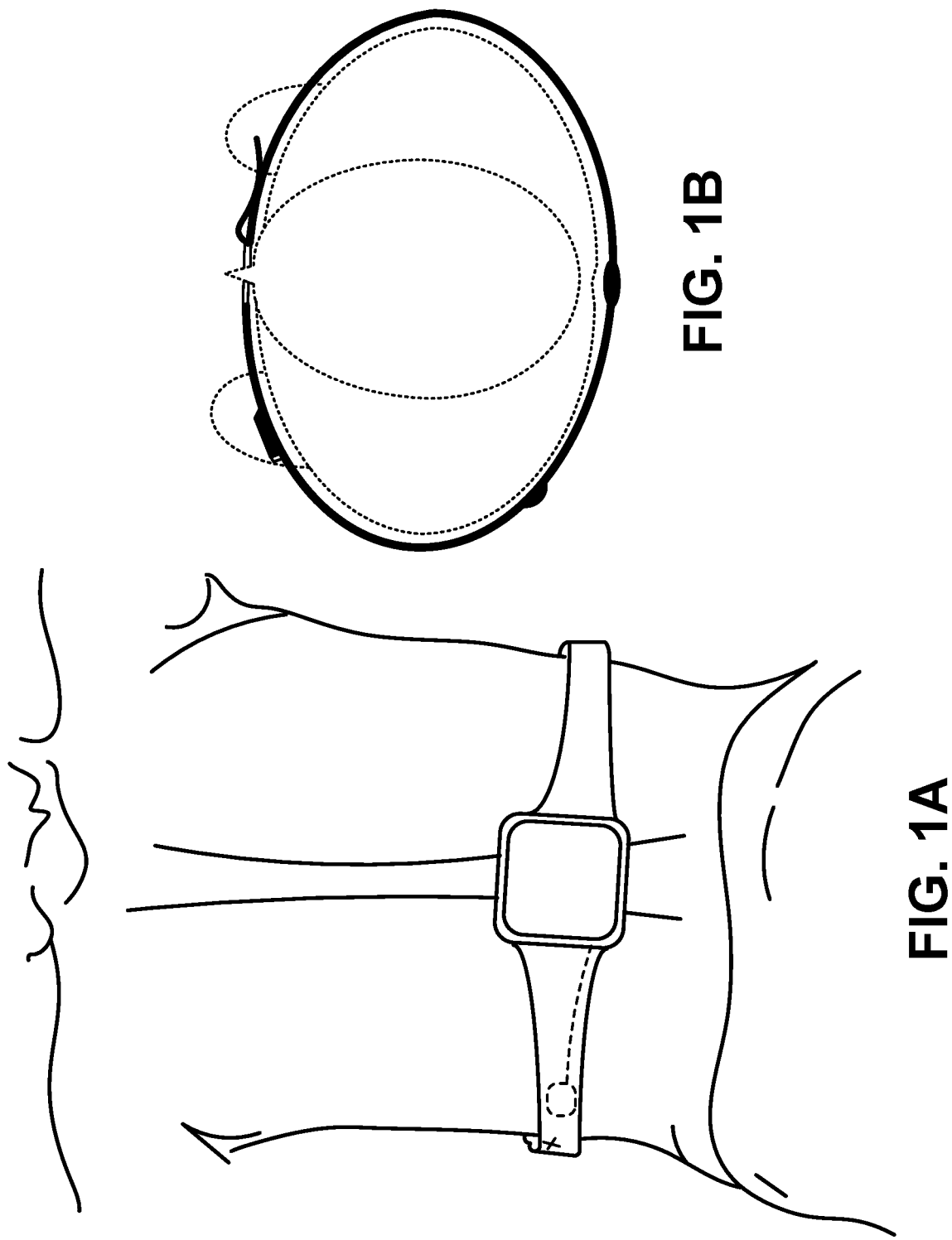
FIG. 1A depicts the wearable antenna assembly placed on the waist of a patient.
FIG. 1B shows the top view of a wearable antenna assembly on a patient.

FIG. 1A shows an example of a wearable antenna assembly (WAA) on a patient. The wearable antenna assembly includes a soft flexible belt, an adjustable strap, and a replaceable battery, an embedded control panel with interface buttons, an embedded microwave field stimulator (MFS), an embedded flexible transmitting antenna, and cabling. In the example, the wearable antenna assembly is secured around the waist of a patient, or an animal. The wearable antenna assembly can be placed around the body at the horizontal vertebrae levels ranging from L5 to T5. The wearable antenna assembly has an adjustable circumferential length from about 22 inches to about 50 inches. Examples of a microwave field stimulator, transmitting antenna, and corresponding implantable neural stimulator with receiving antenna are described in U.S. patent application Ser. No. 13/584,618, title "Microwave Field Stimulator," which is incorporated herein by reference.

The microwave field stimulator attached to the wearable antenna assembly is powered by a replaceable battery and controlled by an embedded control panel. The replaceable battery is comprised of rechargeable battery chemistry; such as, but not limited to lithium-ion, lithium polymer, nickel cadmium, nickel metal-hydride, etc. The replaceable battery can have a capacity within a range from 0 mAh to 10,000 mAh. The replaceable battery can have a nominal voltage rating from about 1.0 volt to 20 volts. In certain embodiments, the replaceable battery can be embedded within the wearable antenna assembly and recharged via a wall plug or with wirelessly.

The microwave field stimulator is connected to the embedded transmitting antenna, which transmits a radio frequency (RF) signal to an implanted receiving antenna within the tissue of the patient, on the skin of the patient, or within an article of clothing close to the body of the patient. The RF signal may have a characteristic frequency within a range from about 800 MHz to about 6 GHz. The embedded transmitting antenna embodied in FIG. 1A is a directional patch antenna, but other antenna types can be used; such as a monopole, dipole, yagi, whip, or horn antenna.

FIG. 1B illustrates the top view of a wearable antenna assembly on a patient. The embedded control panel, embedded microwave field stimulator, and the embedded transmitting antenna are flexible and can conform to the shape of the patient's back. The microwave field stimulator and the transmitting antenna are low profile and streamlined to contour with the patient's body curves. This low profile allows the patient to conceal the wearable antenna assembly under clothing easily.

Figure 2:
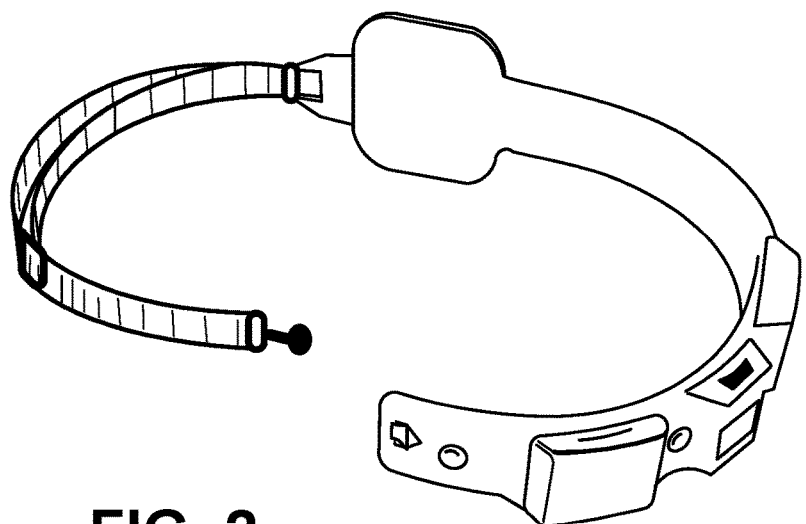
FIG. 2 illustrates a three dimensional view of a wearable antenna assembly.

FIG. 2 shows a three dimensional view of a wearable antenna assembly. The adjustable strap can be made of stretchable, supporting material such as elastic or nylon. The adjustable strap can be removed from the wearable antenna assembly to be washed and replaced with an adjustable strap that is either shorter or longer. The width of the adjustable strap can be within a range from about 0.2 inches to about 5.0 inches. The circumferential length of the adjustable strap can be within a range from about 10 inches to about 60 inches. As shown in FIG. 2, the adjustable strap uses connector tabs that pull through an open slot on the structural wearable antenna assembly and are rotated to lock into place.

The structural wearable antenna assembly holds the battery, embedded control panel, embedded microwave field stimulator, and the embedded transmitting antenna. The structural wearable antenna assembly can be made of flexible, semi-rigid materials such as elastomers, rubber, neoprene, and polyurethane. The structural wearable antenna assembly can have a width within a range from 0.2 inch to 5.0 inches. The structural wearable antenna assembly can have a thickness within a range of about 0.1 inches to about 2 inches. The length of the structural wearable antenna assembly can be within a range of about 5 inches to about 20 inches.

The microwave field stimulator can be located within a range from about 0.5 inch to about 12 inches from the embedded transmitting antenna. The thickness of the microwave field stimulator can be within a range from about 0.08 inches to about 0.39 inches. The length of the microwave field stimulator can be within a range from about 0.78 inches to about 2.75 inches. The width of the microwave field stimulator can be within a range from about 0.78 inches to about 2.75 inches.

The embedded transmitting antenna can have a length and width within a range from about 2 inches to 7 inches. The embedded transmitting antenna can have a thickness within a range from about 0.08 inches to about 0.2 inches.

Figure 3A:
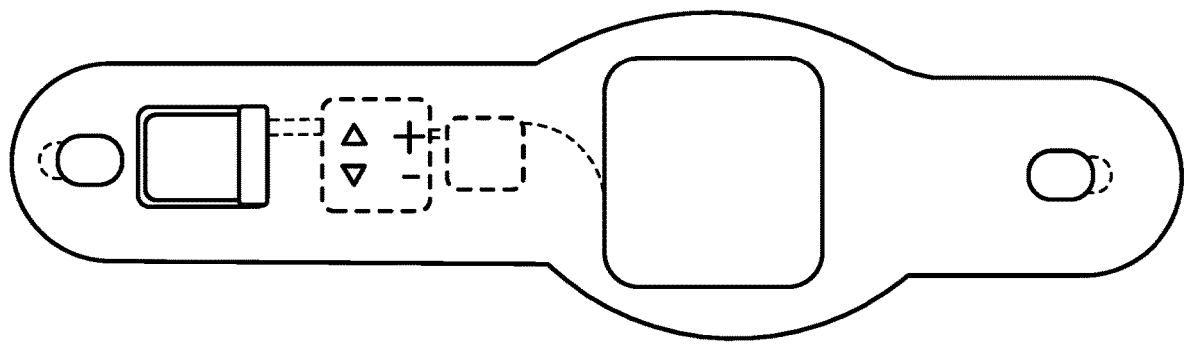
FIGS. 3A and 3B show examples of a static length structural belt.
Figure 3B:

FIGS. 3A and 3B show examples of a static length structural wearable antenna assembly. A structural wearable antenna assembly may include locking slots for an adjustable strap, a replaceable battery, embedded flat wire connectors, an embedded user interface control panel, an embedded microwave field stimulator, an embedded coaxial cable, and an embedded transmitting antenna.

As illustrated by FIG. 3A, the top view of the structural wearable antenna assembly. The replaceable battery is connected to a battery dock that secures the battery. The battery dock uses flat wires that are embedded into the structural wearable antenna assembly to bring power through the control panel and to the microwave field stimulator. The control panel also utilizes multiple flat wires to connect to the microwave field stimulator. The microwave field stimulator outputs an RF signal through the thin profile coaxial cable that is embedded in the structural wearable antenna assembly to the transmitting antenna.

The locking slots are located at opposite horizontal ends of the wearable antenna assembly and connect to an adjustable strap to allow for greater flexibility between patients of different waist sizes.

As illustrated by FIG. 3B, the profile view of the structural wearable antenna assembly. The replaceable battery is locked into the embedded dock. The control panel shows very low profile buttons that are used to control the microwave field stimulator. The microwave field stimulator and embedded antenna show a veil low profile that allows the device to conform well to the patient and remove obstructive extrusions. Structural belt has conforming curves that allow the transitions of thicknesses of the various components to be smoothed out. The conforming curves aid the patient in avoiding the belt getting caught onto corners and edges of objects that a patient may daily interact with.

Figure 4A:
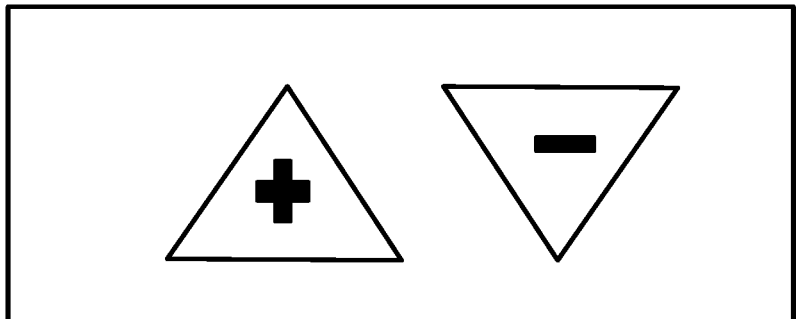
FIGS. 4A, 4B, 4C show various options for a control panel on a wearable antenna assembly.
Figure 4B:
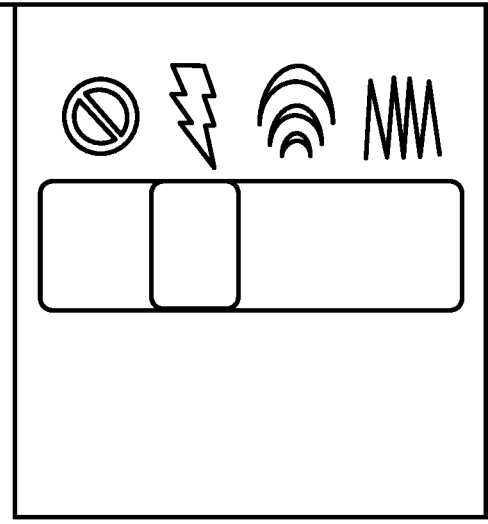
Figure 4C:
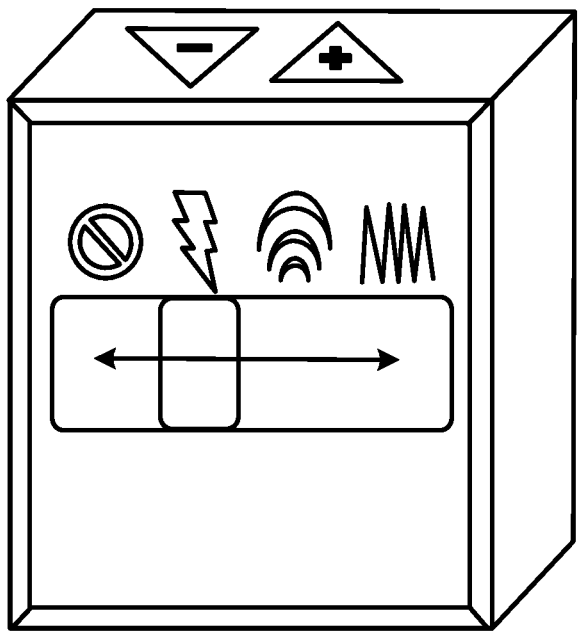

FIGS. 4A, 4B, 4C show examples of a control panel for the WAA. A control panel may include button-switches to control neurostimulation settings, and a sliding switch that chooses the setting that is being controlled by the switches.

As illustrated in FIG. 4A, the WAA may include only two button-switches. These two-button switches may control the amplitude, pulse width, frequency, or preset programs of stimulation. The switches can be labeled with directional arrows or plus and minus features. In certain embodiments, there may be more than two button-switches that can control a number of parameters from the microwave field stimulator.

These soft button-switches, allow the user to increase (+) or decrease (−) the amplitude of the parameter. In certain embodiments, the soft buttons are placed at the top of the belt, allowing the user to see the buttons and select the correct change for the selected parameter. The soft buttons also feature an embossed + and − so that the user can develop a sensory adaption to the parameter change button without relying on sight.

As illustrated in FIG. 4B, the WAA may include a sliding switch that chooses the setting that is being controlled by the switches. The sliding switch can act as an on/off toggle, in this embodiment the slider is pushed all the way to one end, which interrupts all power and stops stimulation. The sliding switch, when not in the off position, will begin stimulation. The slider can toggle button-switches to adjust specific parameters such as amplitude of power, pulse width, frequency, or preset parameters. The toggle switch is positioned in the front face of the belt, which allows the user to see the switch or rely on sensory feedback of the switches resistance to being thrown into position.

As illustrated in FIG. 4C, the control panel is streamlined and integrated into the belt. This module is positioned between the microwave field stimulator and the battery on the belt and is accessible at the front of the belt. The user can use tactical sensory feedback when operating the control panel. The toggle switch and the soft buttons make the control panel distinguishable from the microwave field stimulator and the battery. The control panel's width and length can be within the range from about 0.5 inches to about 2.0 inches. The control panel's thickness can be within the range from about 0.08 inches to about 0.5 inches. In certain embodiments, the control panel may have multiple indicator lights used to inform the user of system functions.

Figure 5:
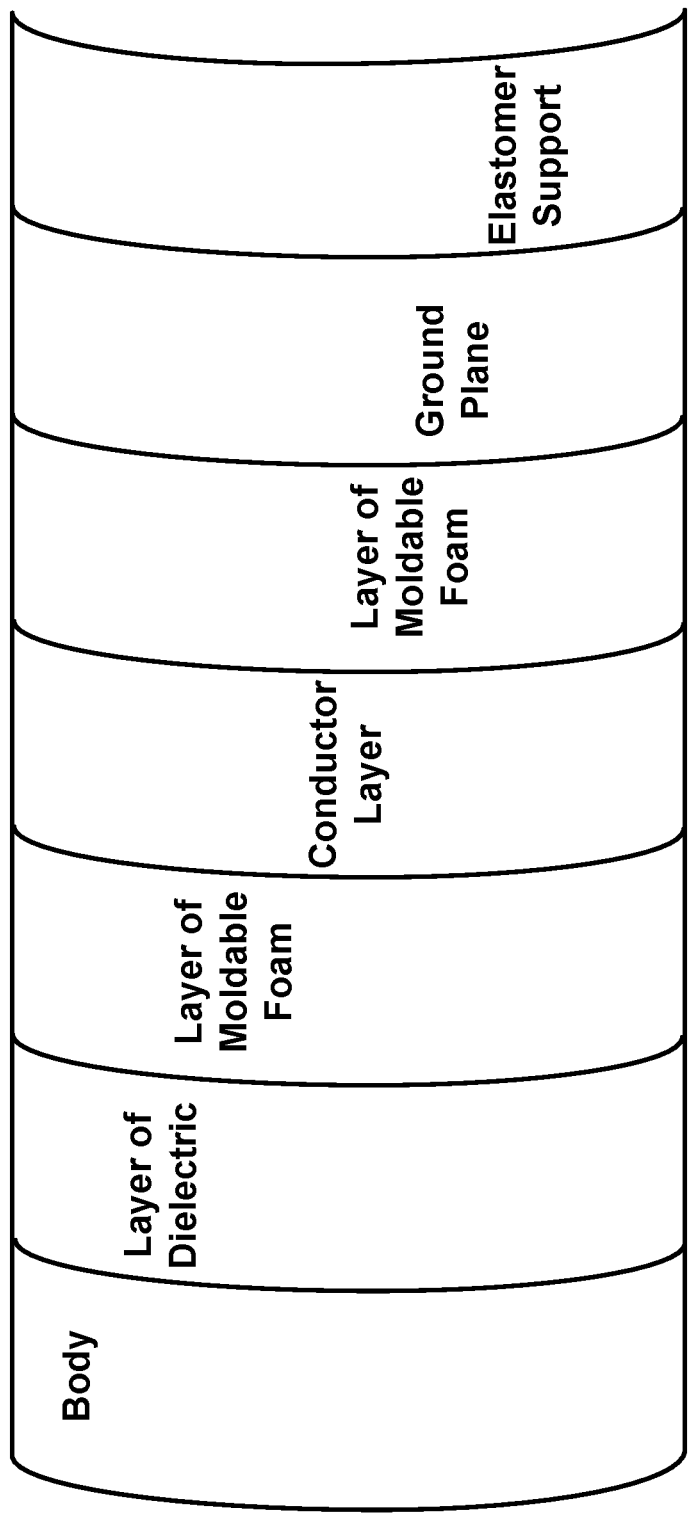
FIG. 5 depicts an example block diagram of the structural layers of a flexible transmitting antenna.

FIG. 5 depicts a block diagram of the structural layers of a flexible transmitting antenna. The flexible transmitting antenna is composed of a conductive layer pitted between equal layers of moldable foam with a ground plane and a dielectric matching layer that is placed against the back of the user. The transmitting antenna is tuned with a dielectric material to match the coupling of the user's skin eliminating the need for a gel to facilitate transmission.

As shown in FIG. 5, the conductive layer of the transmitting antenna is composed of a conductive material such as copper, gold, etc. The foam layers are comprised of non-conductive materials such as polyimide and secured to the conductive layer with a thin layer of adhesive. The antenna is capable of transmitting energy through the body to the implanted lead because of the dielectric matching layer. This layer is affixed to the transmitting antenna and is in contact with the body while the WAA is worn. The antenna can be comprised of a conductive layer pitted between two layers of moldable foam. This antenna construction permits the antenna to be shaped and formed to fit flush against the back of the user eliminating air gaps. The ability of the dielectric to match the permittivity of the body allows the antenna to perform without the assistance of a gel applied to the body to maintain contact between the skin and the antenna.

Figure 6:
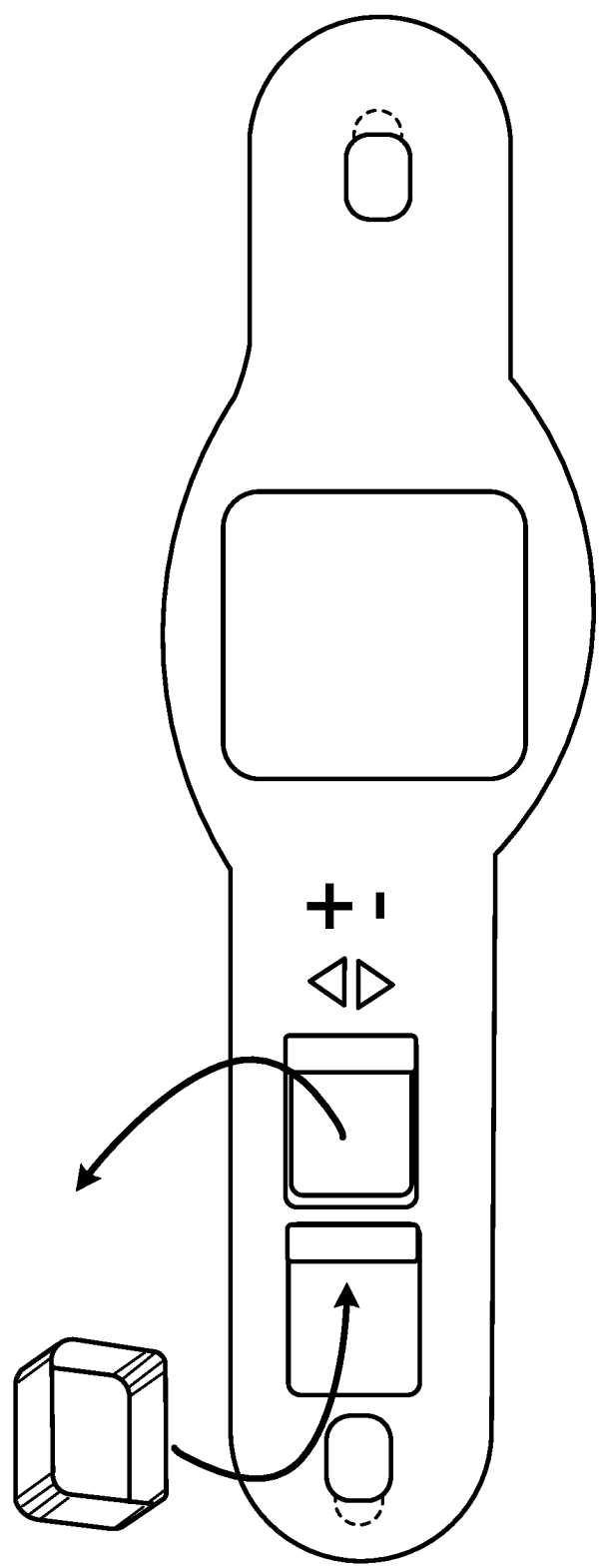
FIG. 6 illustrates a wearable antenna assembly with a secondary battery dock.

FIG. 6 illustrates a design of the WAA to have a secondary battery dock which allows the user to hot-swap batteries for continuous neurostimulation. A WAA may consist of two embedded battery-docking stations. Once the primary battery connected to the MFS is close to drained and the user is informed via LED or notification to smart phone via Bluetooth, the user can place a fully charged secondary replaceable battery into the secondary battery dock to continue stimulation. The user can disengage the drained battery from the belt, once the fully charged battery is in place. The belt-mounted secondary battery dock is positioned next to the primary battery-dock on the user's front side of the belt.

The stationary battery docks' connections can be placed in parallel so that the voltage to the MFS is not doubled, but rather the capacity is increased. In certain embodiments, a user can have both the primary battery and secondary battery engaged on the WAA to extend the overall charge life of the device.

Figure 7:
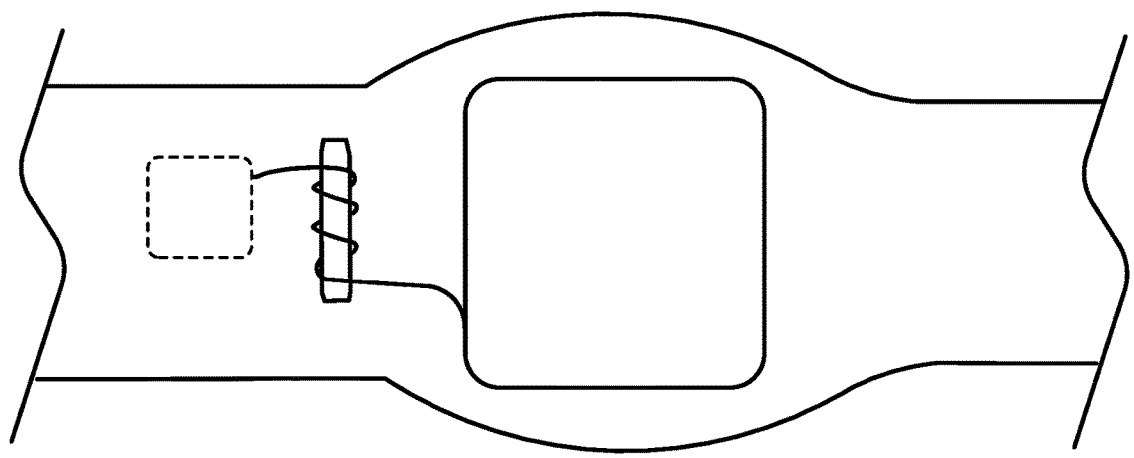
FIG. 7 illustrates adjustable cabling for circumferential adjustability of the wearable antenna assembly.

FIG. 7 illustrates an adjustable coaxial cabling method used for circumferential length adjustability of the structural belt. This embodiment of the structural belt includes a microwave field stimulator that can be moved along the circumferential axis of the belt, while the embedded antenna is stationary. The coaxial cable is wound around a small flexible rod that is secured to the structural belt at one end. The rod releases wound cable at one end, allowing the user to wind or unwind the cabling from the rod and adjust the location of the microwave field stimulator for best comfort. The amount of adjustable length added from the rod can be within the range from about 0.5 inches to about 6.0 inches.

Figure 8:
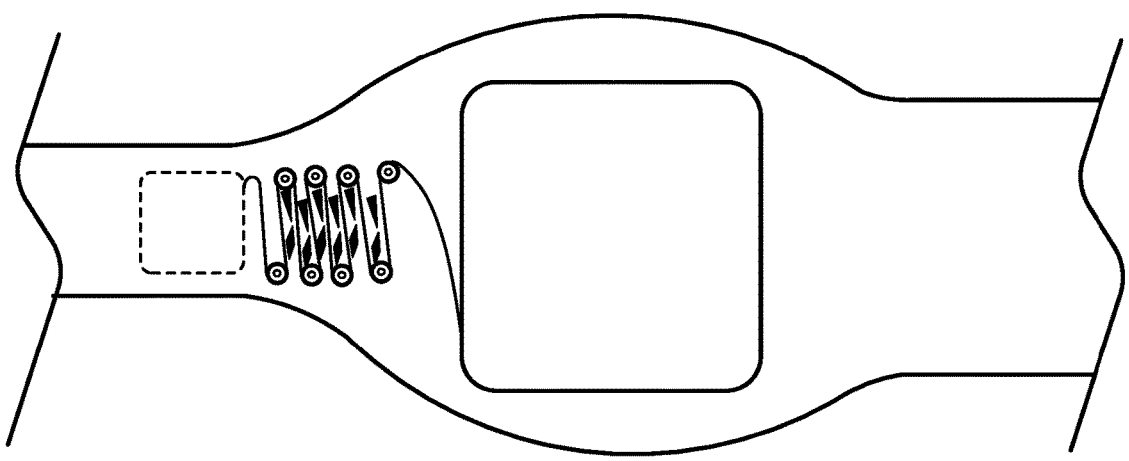
FIG. 8 illustrates adjustable cabling in a flexible wearable antenna assembly to allow for stretch flexibility.

FIG. 8 illustrates an adjustable coaxial cabling method in a flexible structural belt to allow flexibility when the belt is stretched. A flexible structural belt can maintain the integrity of the coaxial cable's connectors when the patient is stretching the WAA around the waist. The coaxial cable is wrapped around cleats that are attached to multiple scissor hinges. The scissor hinges are mounted to the flexible structural belt, and when stretched the scissor hinges expand and the cabling woven over the cleats is elongated. The cleat-scissor mechanism allows circumferential length adjustability from about 0.01 inches to about 2.0 inches.

FIGS. 9A to 9E demonstrate the tensioners used to ensure that shape of an embedded antenna is maintained while the belt is worn by the user.

FIG. 9A illustrates an embedded antenna while the pull-string tensioners are not engaged and the embedded antenna is flat. When the two strings are pulled tight, the low-profile cleats pull the structural belt together to push the embedded antenna convexly into the crevice of the lumbar region of the patient, as depicted in FIG. 9C. The locking modules hold the strings in place so that the tension is maintained, as depicted in FIG. 9B.

FIG. 9B illustrates an embedded antenna while the pull-string tensioners are engaged and the embedded antenna's flexible shape is maintained.

FIG. 9C illustrates a WAA on a patient where the pull-string tensioners are engaged and the embedded antenna's flexible shape conforms to the lumbar crevice of the patient.

FIG. 9D illustrates an embedded antenna while the Velcro straps are not engaged and the embedded antenna's flexible shape is not maintained. When the Velcro straps are connected, the sewn-in anchors of each strap pull the structural belt together to push the embedded antenna convexly into the crevice of the lumbar region of the patient.

FIG. 9E illustrates an embedded antenna while the Velcro straps are engaged and the embedded antenna's flexible shape is maintained.

FIG. 10A illustrates a WAA with a two-piece antenna with interlocking fingers that give greater conformity to the lumbar crevice. The interlocking fingers of the antenna automatically adjust to the patient according to the tightness of the WAA. As the patient tightens or loosens the adjustable portion of the WAA, the interlocking fingers push together to either go convex or concave into the lumbar crevice.

FIG. 10B illustrates a two-piece antenna with interlocking fingers that adjust along the caudal-cranial axis. The antenna is composed of the flexible conductive layer between the two, polyamide foam layers secured with an adhesive. The antenna comprises of two pieces that lock together. The interlocking ends can flex to conform to the crevice of the user's back. The antenna will lock tight, but flexibility of the antenna will be maintained at the ends of the antenna to encourage elimination of air between the antenna and the user's back.

Figure 11:
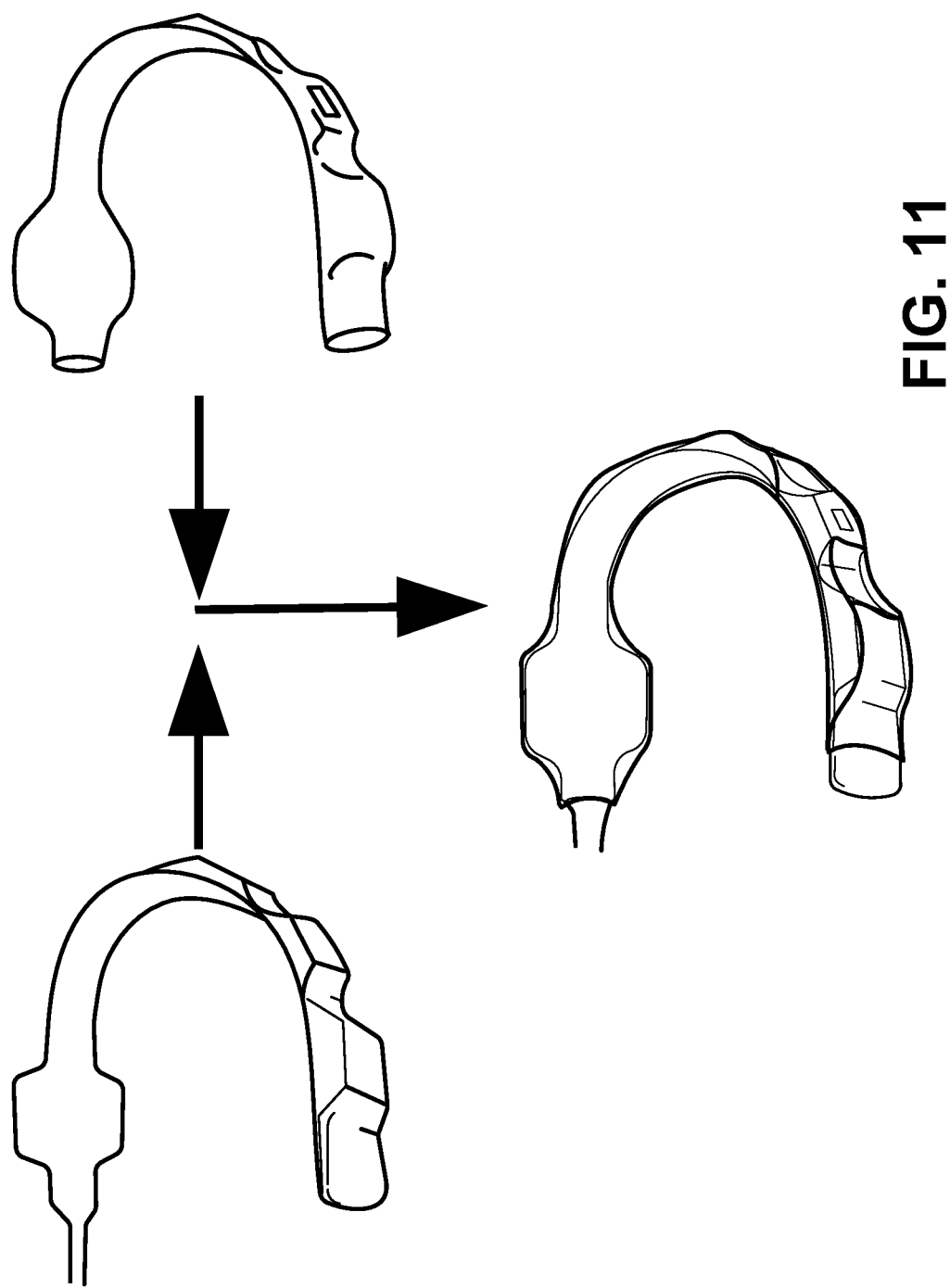
FIG. 11 demonstrates the use of a soft sleeve that is slipped over the structural portions of the wearable antenna assembly.

FIG. 11 demonstrates the use of a soft sleeve that is slipped over the structural portions of the WAA. The sleeve has an opening at each end and shaped to identify the end that is intended for the antenna and an opening for the toggle switch of the control module. The sleeve is tubular, designed to fit tightly to the structural belt and to provide additional cushioning for user comfort. Additionally, this tight fitting sleeve streamlines the modules of the belt for concealing the belt under clothing. The sleeve material can be a water resistant, soft, flexible material such as neoprene or nylon with elastic support threads. The sleeve is machine washable.

Figure 12:
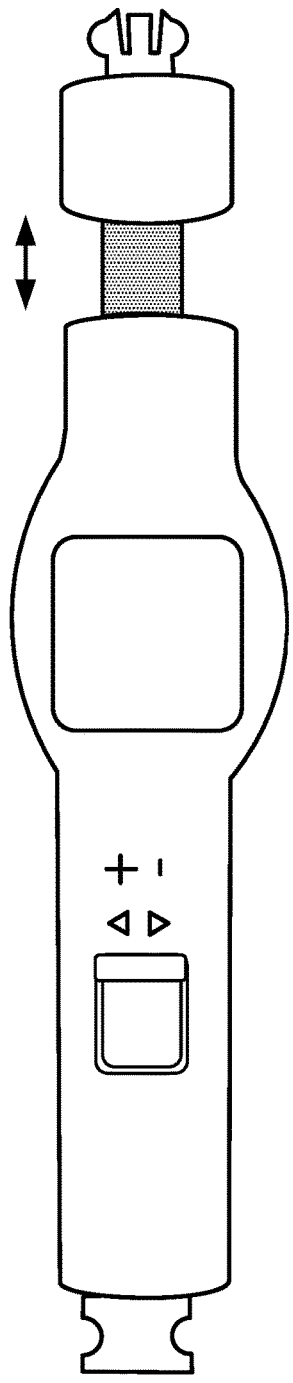
FIG. 12 illustrates an embodiment of the wearable antenna assembly with an elastic portion to increase flexibility.

FIG. 12 demonstrates the implementation of an elastic portion into a structural belt to increase flexibility between user positions. This WAA uses snap-in connectors to secure the structural belt around the user. The adjustability of the WAA is isolated to only one side of the belt allowing the user to easily adjust the fit of the belt for comfort, and removal when necessary. The user of a singular point of adjustability eliminates user errors, or risk of incorrectly adjusting the belt on the body. The combination of elasticity and adjustability provides secure fit of the belt to the body when the user is changing positions, i.e. standing to sitting, standing to bending over, sitting to bending over, etc.

Figure 13:
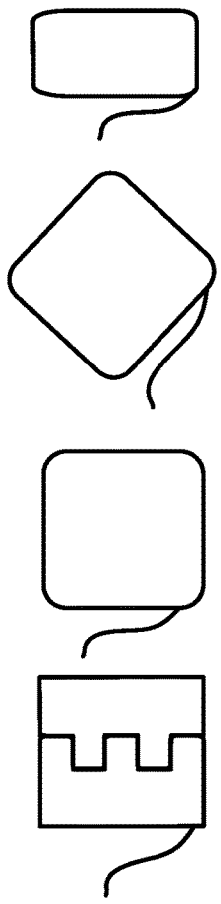
FIG. 13 illustrates various embodiments of flexible transmitting antenna shapes for the wearable antenna assembly.

FIG. 13 illustrates various patch antenna shapes that can be used in the wearable antenna assembly. The interlocking fingers antenna, square antenna, diamond antenna, and rectangular antenna are examples of antennas for the WAA.

Figure 14:
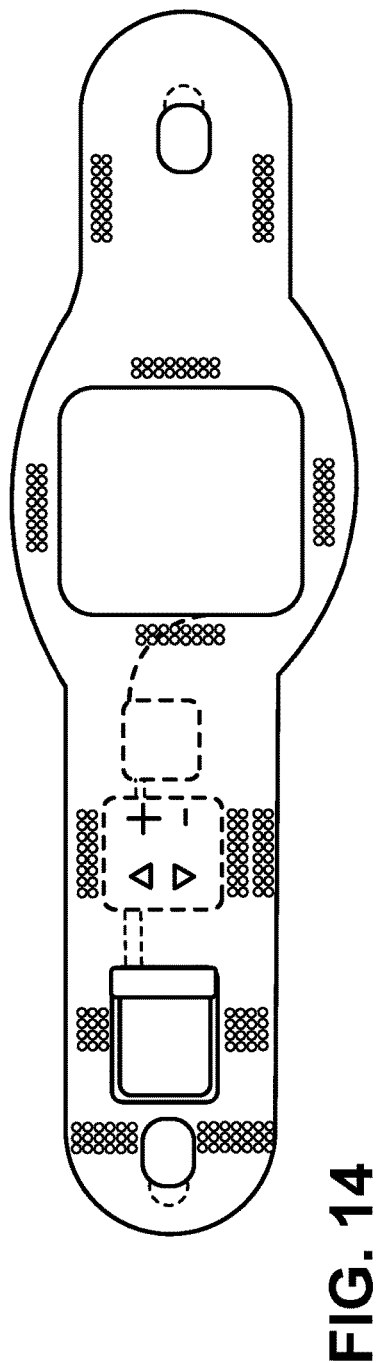
FIG. 14 depicts the use of venting holes in the wearable antenna assembly for evaporation of sweat and increased breathability.

FIG. 14 depicts the use of venting holes in the wearable antenna assembly to encourage the evaporation of sweat and increase the breathability of the assembly. The structural belt has perforations in the elastomer to permit airflow to the skin. The ventilation holes permit the flow of air to the covered area of the skin, which allows natural body perspiration to cool the surface temperature. The holes are placed at modules that are potential heat generating modules to ventilate the areas that are more susceptible to perspiration.

Figure 15:
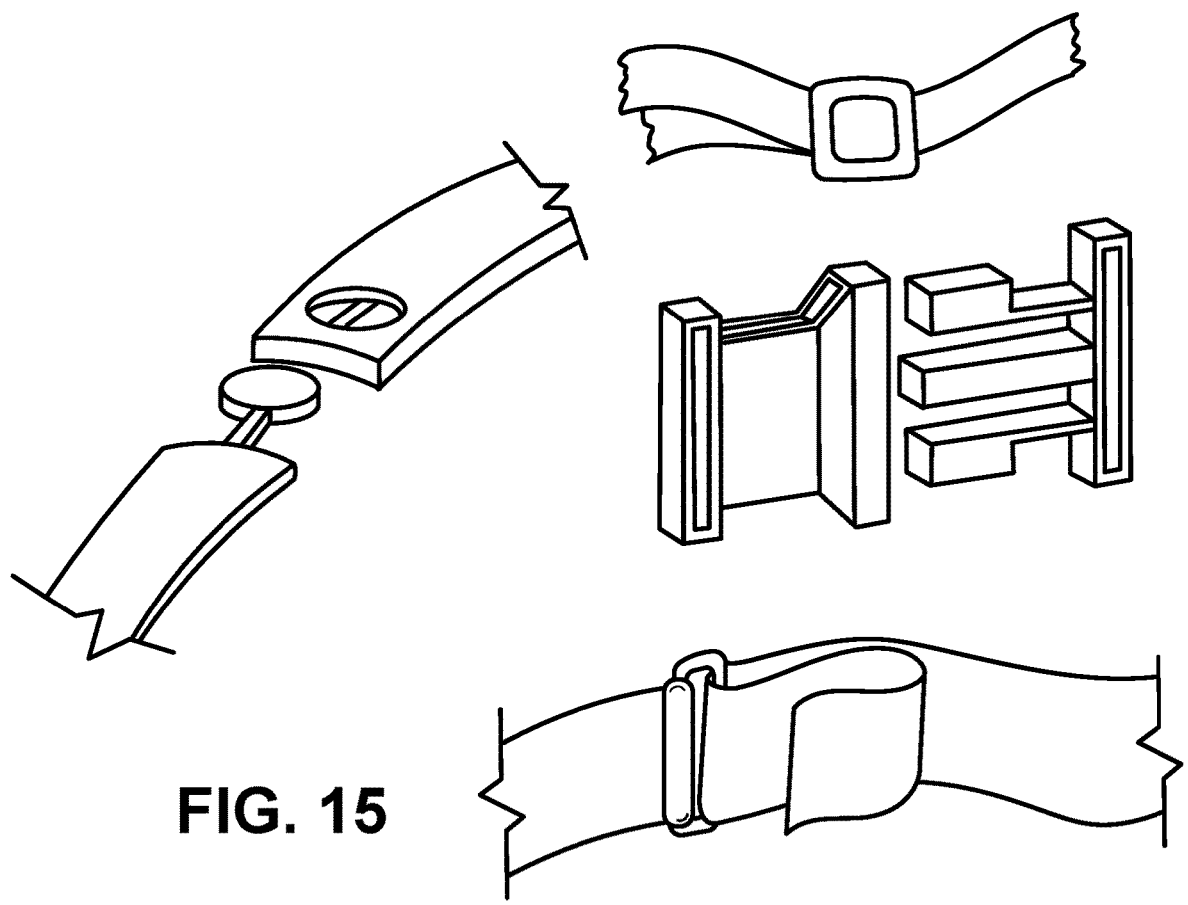
FIG. 15 is an example of fasteners used to secure the wearable antenna assembly to the patient.

FIG. 15 is an example of fasteners used to secure the wearable antenna assembly to the patient. Locking fasteners such as a tab-slot hole design, a parachute clip, or a velcro strap may be used on the WAA. A sliding clip can be used to adjust the circumference of the WAA. The fastening methods are easily operated while the belt is worn on the body. The fastener will be secured at the front and adjusted at the side of the user, which should not impede dexterity when attempting to remove or adjust the fit of the belt.

Figure 16:
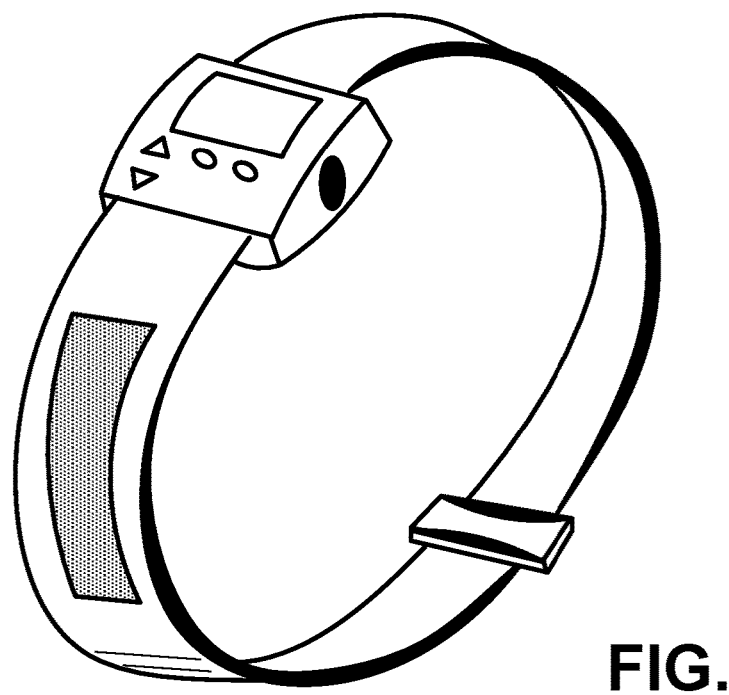
FIG. 16 illustrates a wearable antenna assembly that is condensed to fit into the shape of a standard watch.

FIG. 16 illustrates a wearable antenna assembly that is condensed to fit into the shape of a standard watch. A watch that contains an embedded antenna, microwave field stimulator, button controls, and replaceable battery can be used to deliver RF to an implanted lead module for peripheral nerve stimulation. The transmitting antenna is formed into the straps of the watch, with the microwave field stimulator, battery, and button controls are incorporated into the face of the watch. The wristwatch may have an LCD display screen that will visually communicate the stimulation, pulse width, and frequency parameters for the user to update with the buttons, and have functionality similar to standard watches including time, stopwatch, countdown timer, alarm, date, etc.

Figure 17:
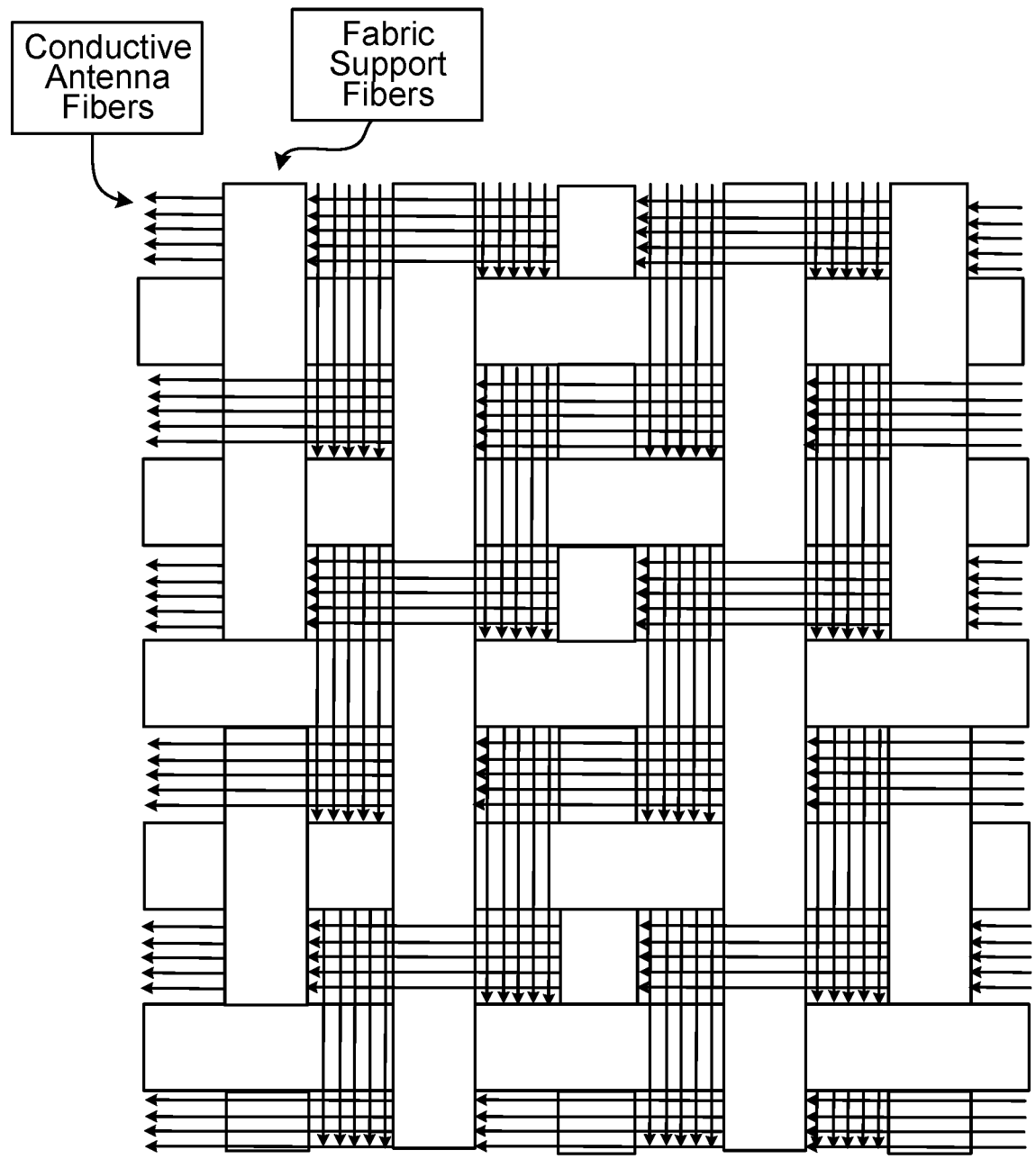
FIG. 17 illustrates a fabric-antenna made of micro-conducting fibers woven into a structure of fabric to create a flexible antenna.

FIG. 17 illustrates a fabric-antenna made of micro-conducting fibers woven into a structure of fabric to create a flexible antenna. The conductive threads can be made of conductive materials such as gold, copper, etc. The conductive threads are woven into fabric threading to create a flexible and thin patch of conductive material. For tuning of the antenna to specific frequencies, the material would be trimmed or cut to the required length. The conductive fabric is then used transmit an RF signal directly to the implant at various locations on the body where fabric is found, including but not limited to: lumbar, thorax, stomach, chest, shoulder, arm, forearm, leg, foot, hand, neck, buttocks, etc. The microwave field stimulator would be implemented into a separate belt or clip that is held comfortably at the waist or in the pocket.

Figure 18A:
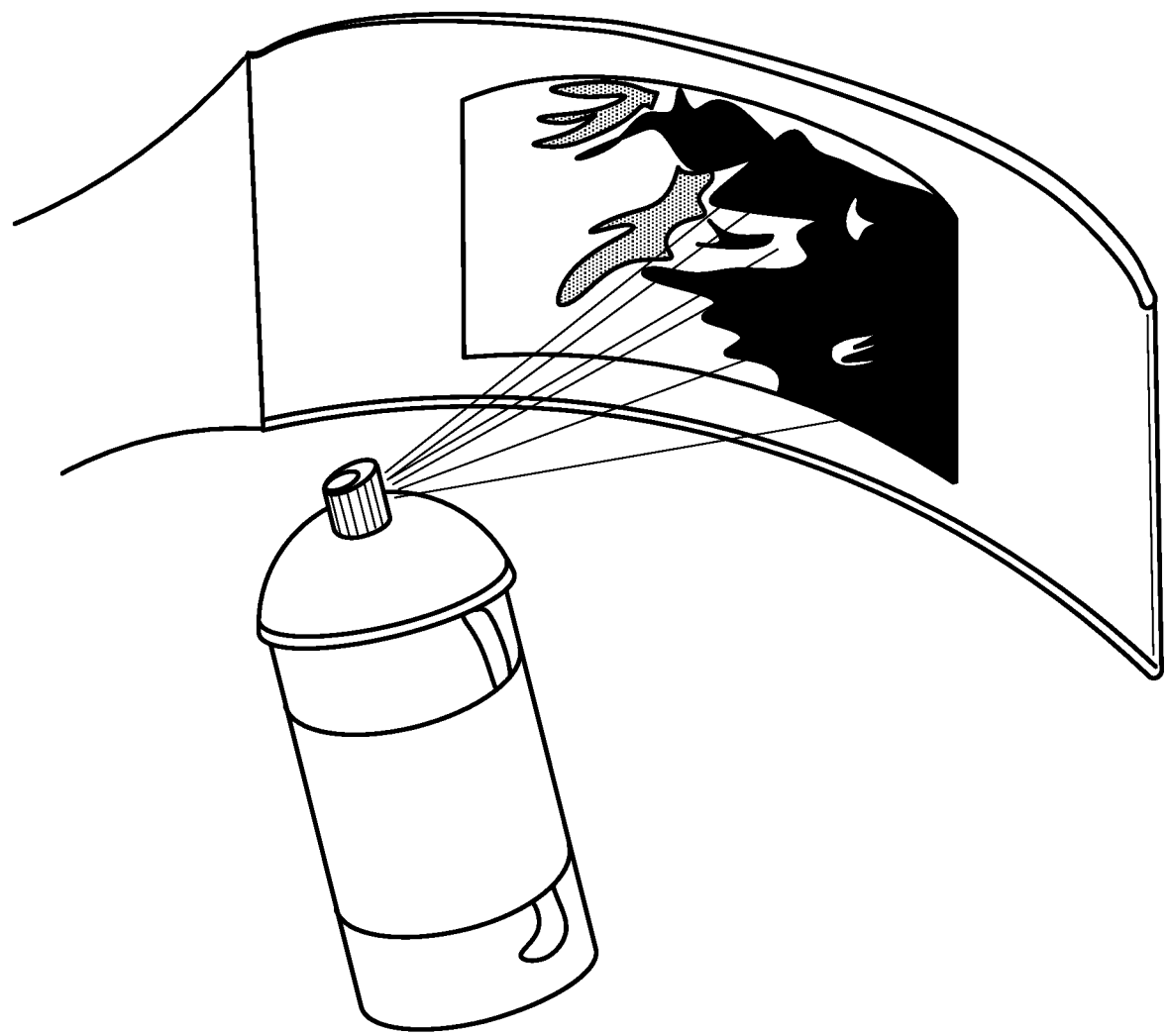
FIG. 18A-B illustrates the flexible transmitting antenna within the wearable antenna assembly.

FIGS. 18A and B illustrate the implementation of an antenna that is deposited into a WAA.

FIG. 18A illustrates the process of depositing materials to create the antenna stackup. The structural belt is sprayed with micro-drops of a liquid contained under pressure for precise placement. The deposit made by these liquids once dry will form the dielectric and conductive materials of the antenna. This eliminates the need for pitting the antenna into the belt. The cabling is run through the belt with a coaxial cable connecting to a copper or gold connector built into the belt. Once sprayed with the liquid, the antenna will be affixed to the coaxial cable.

Figure 18B:
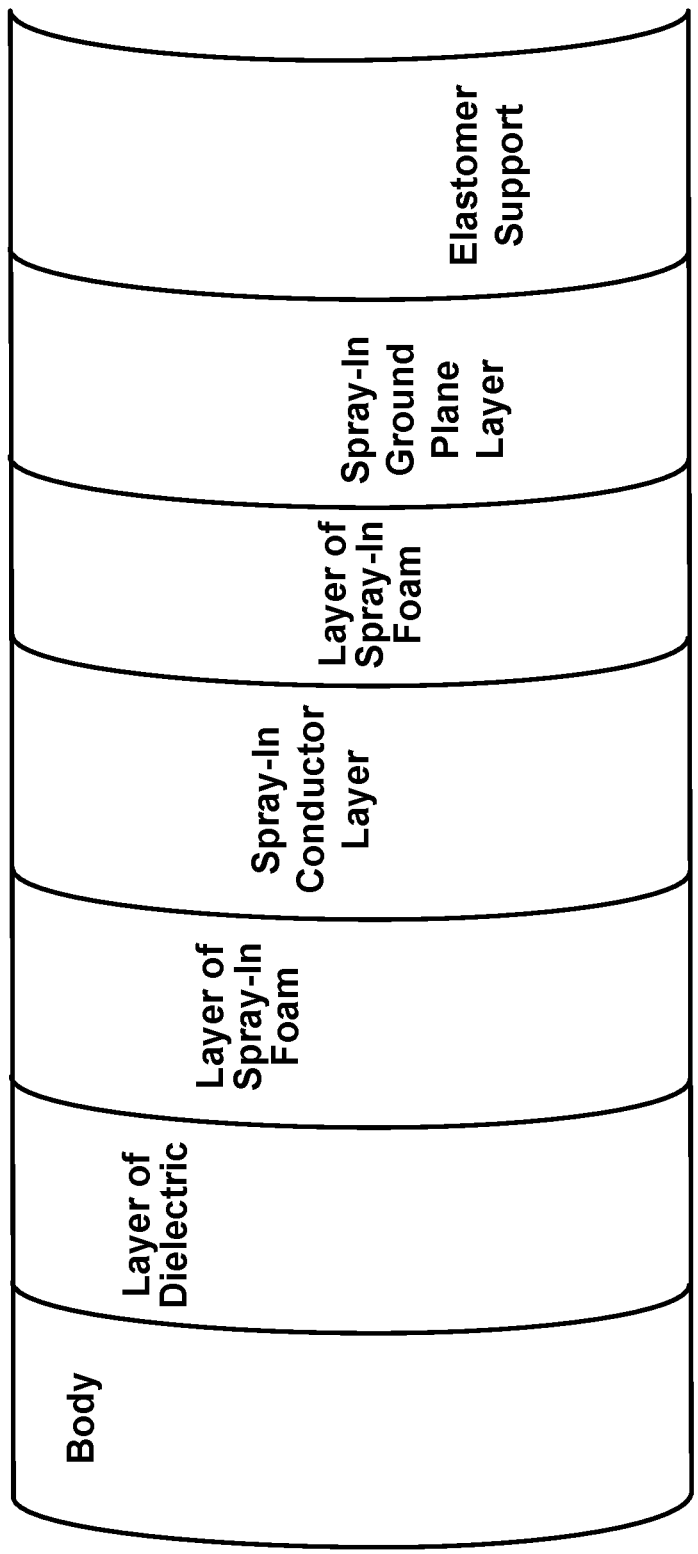

FIG. 18B is a block diagram depicting the antenna layers for an assembly where the dielectric, conducting planes, and foam are deposited in to create an ultra thin profile. The transmitting antenna is spray molded into the structural belt through spraying in the layers of the antenna to form the antenna to the exact shape of the belt. The conductive ground layer is sprayed in first, followed by the layer of sprayed polyamide foam. Once dry the conductive layer is sprayed in followed by a second layer of polyamide foam. Once dry, the matching dielectric layer is laid over the sprayed antenna concealing the antenna from the user. The cabling is run through the belt with the coaxial cable connecting to a copper or gold connector built into the belt. Once sprayed with the conductive liquid, the antenna will be affixed to the coaxial cable.

Figure 19:
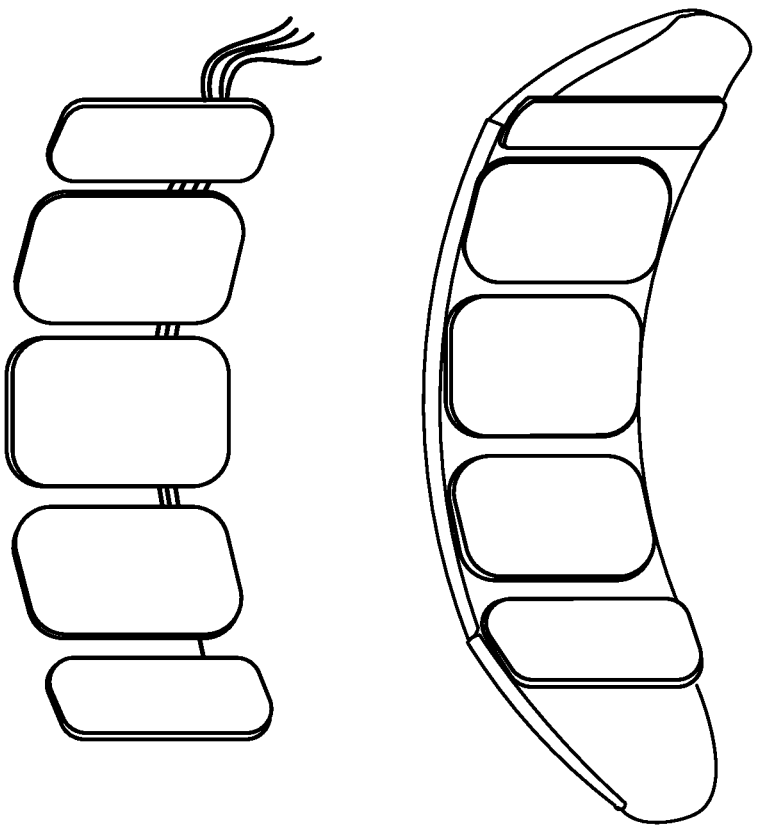
FIG. 19 illustrates a semi-cylindrical array of antennas that are used to transmit power.

FIG. 19 illustrates a semi-cylindrical array of antennas that are used to transmit power to the implant. The semi-cylindrical antenna array is comprised of smaller patch antennas that act as a single antenna to transmit RF energy to an implanted lead. The smaller antennas are arranged to direct or steer the energy directly to the implant. The smaller antennas have small space between them to improve the flexibility of the WAA and conformity of the antennas to the body. Each antenna is moldable and would conform to the back and body of the user. The mold-ability of many small antennas improves the ability of the patient to correctly place the belt on the body after removal.

Figure 20:
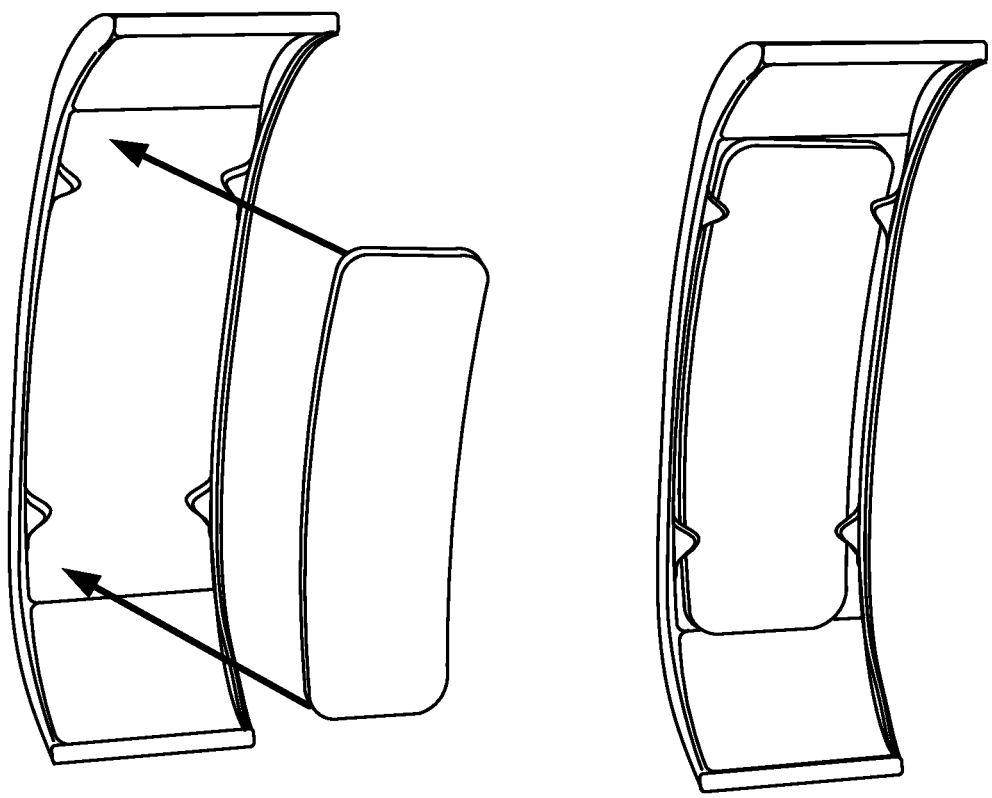
FIG. 20 illustrates a molded flexible transmitting antenna that is snapped into the wearable antenna assembly.

FIG. 20 illustrates a molded antenna that is snapped into the wearable antenna assembly. A snap-in molded antenna is composed of flexible conductive layers pitted between two layers of moldable dielectric foam attached with adhesive. The patch is moldable and attached to the structural belt with elastomer teeth. The antenna can be molded independently from the belt, allowing the user to conform the antenna to their body without the risk of the antenna relaxing its shape due to tension from the belt. The belt will fit snug on the user, while maintaining constant contact of the antenna on the user.

Figure 21:
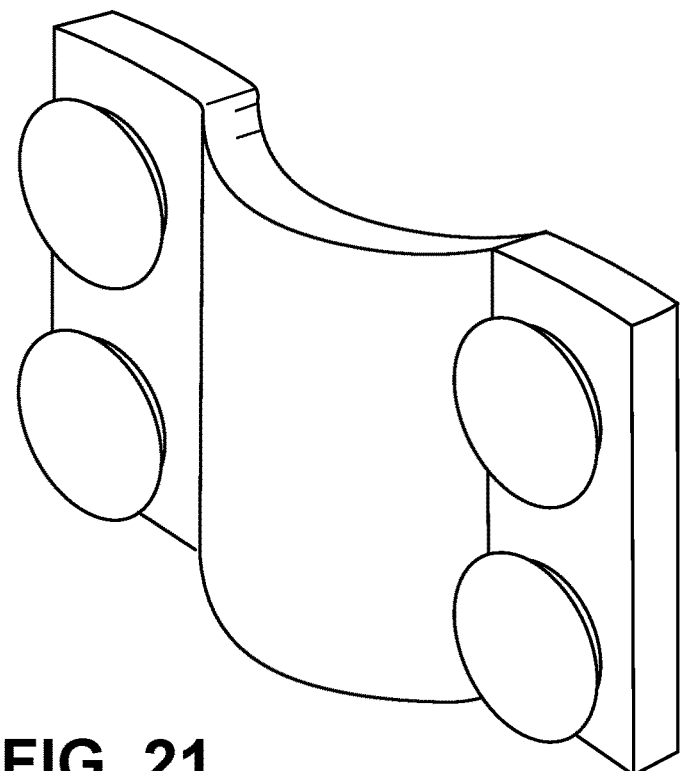
FIG. 21 is an example of a molded flexible transmitting antenna that conforms to the lumbar crevice, and can be secured directly to tissue using suction cups.

FIG. 21 is an example of a molded antenna that conforms to the lumbar crevice, and can be secured directly to tissue using suction cups. The suction-cup antenna is conformed and affixed to the users back with suction cups. The formable antenna is designed with rubber suction cups that are able to attach to the back of the user with applied force, creating a vacuum between the antenna and the user. This gives greater conformity of the transmitting antenna to the user's body and will stabilize the antenna over the implant. The suction-cup antenna is encapsulated with the matching dielectric and is connected via coaxial cable to the microwave field stimulator that is clipped to the belt or in the pocket.

Figure 22:
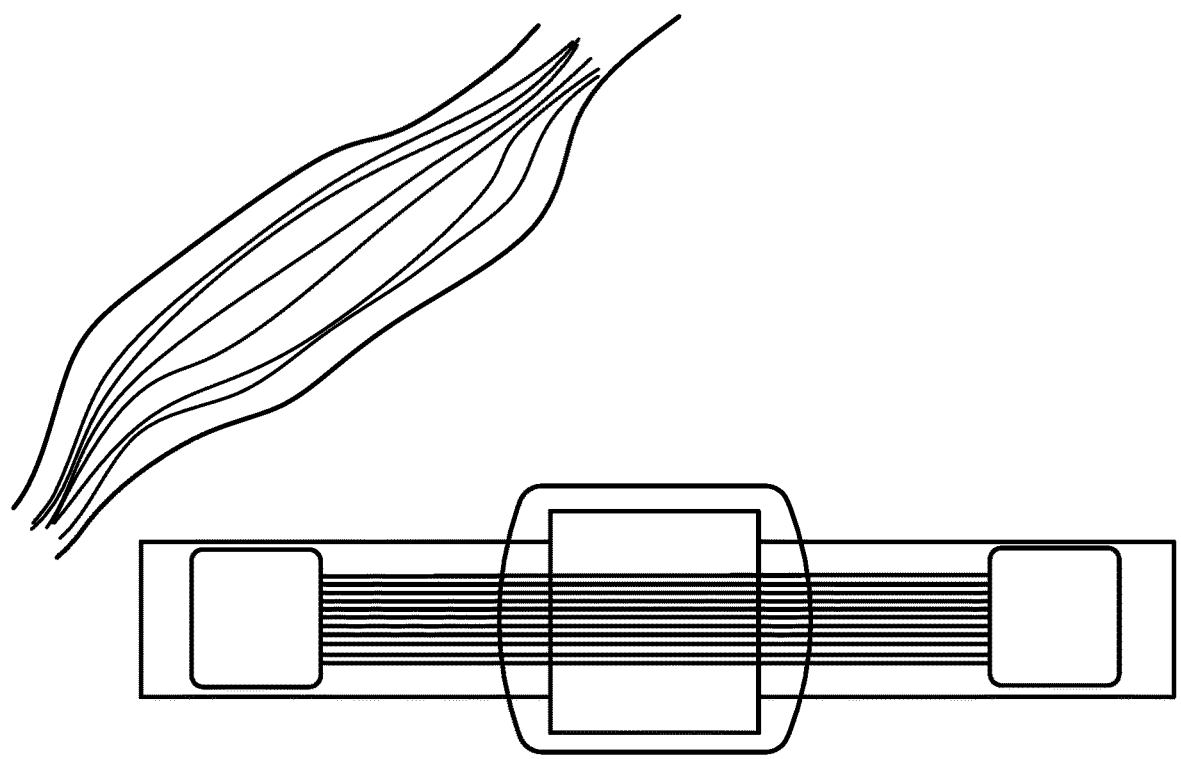
FIG. 22 illustrates fluid wicking, hydrophilic micro-channels built in to the wearable antenna assembly to displace fluids that would otherwise disrupt the tuning of the antenna.

FIG. 22 illustrates fluid wicking, hydrophilic micro-channels built in to the wearable antenna assembly to displace fluids that would otherwise disrupt the tuning of the antenna. The elastomer material of the structural belt may be affixed with moisture pads, made of an absorbent material that is flush with the belt surface. The micro-channels are hydrophilic and draw moisture, such as sweat, away from the antenna face, and direct the moisture through the long narrow channels pitted into the structural belt to the washable moisture pads attached on the inside of the belt. In certain embodiments the water micro-channels would be located around the circumference of the WAA, without the use of moisture pads, to displace moisture to less moist regions of the WAA.

Figure 23:
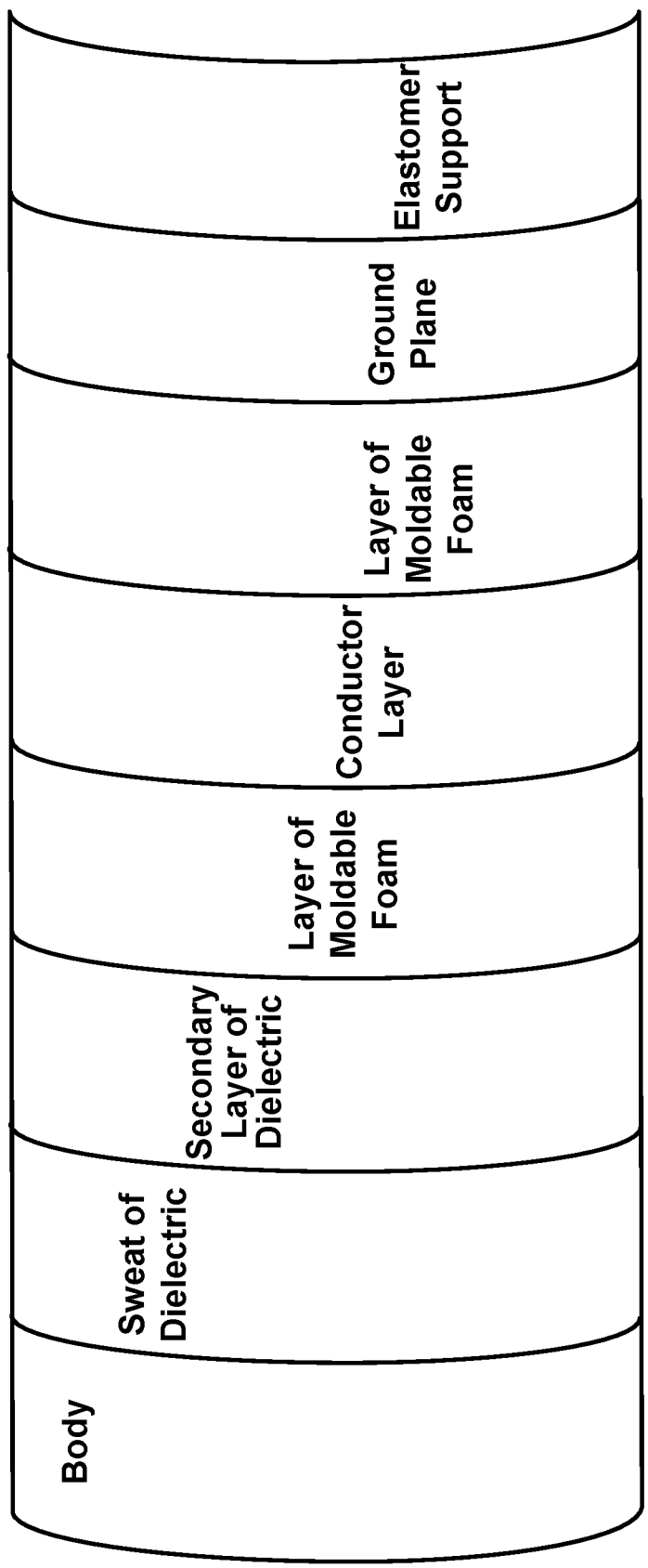
FIG. 23 is a block diagram depicting the antenna layers for an implementation where perspiration is used in the tuning calculation of the dielectric within the wearable antenna assembly.

FIG. 23 is a block diagram depicting the antenna layers for an implementation where perspiration is used in the tuning calculation of the dielectric within the wearable antenna assembly. In this embodiment, the embedded antenna uses the permittivity of sweat as a form of matching dielectric to allow transmission of energy through the body. The secondary layer of matching dielectric is effective for transmission when the body is not perspiring. This layer is similar in permittivity to sweat, but not identical. The embedded antenna is designed with a conductive layer pitted between two layers of moldable foam. The moldable foam allows the antenna to be flexed and molded to match the shape of the users back. This body shaped antenna maintains contact with the skin encouraging body perspiration to match the dielectric for energy transmission.

Figure 24:
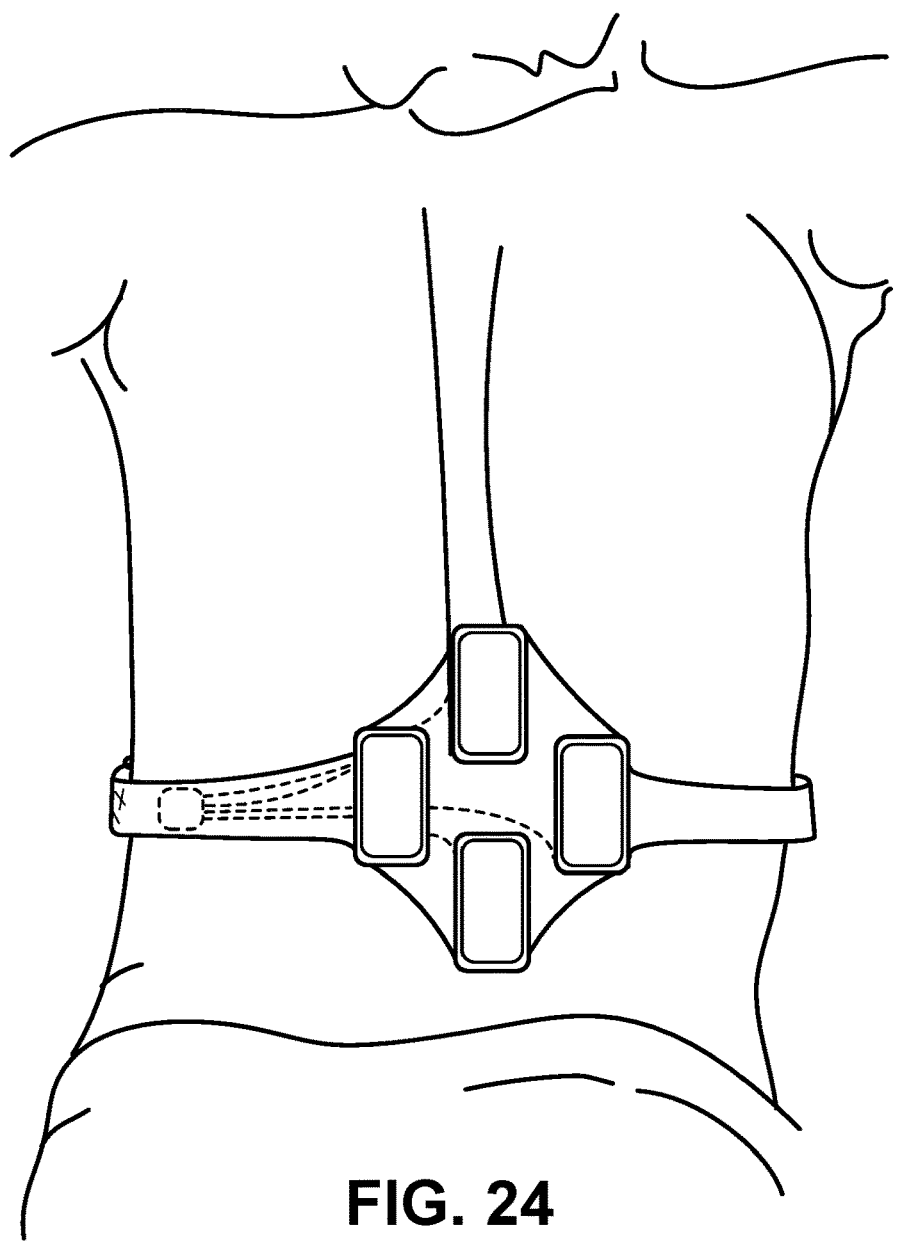
FIG. 24 demonstrates an antenna array that can be used to select the antenna that is in the best position to power the lead and reduce reflection within the wearable antenna assembly.

FIG. 24 demonstrates an antenna array that can be used to select the antenna that is in the best position to power the lead and reduce reflection within the wearable antenna assembly. The WAA is designed to incorporate more than one embedded antenna to power the implanted lead. The transmitting antennas are small and are placed in the structural belt. The microwave field stimulator is able to power one, two, three or all four of the antennas to transmit the RF energy to the lead. The antenna array allows RF energy to be steered towards the implant. The microwave field stimulator can dynamically calculate the antenna that has the least amount of reflected energy and use the most efficient antenna to power the lead as the user moves around in their daily environment.

Figure 25:
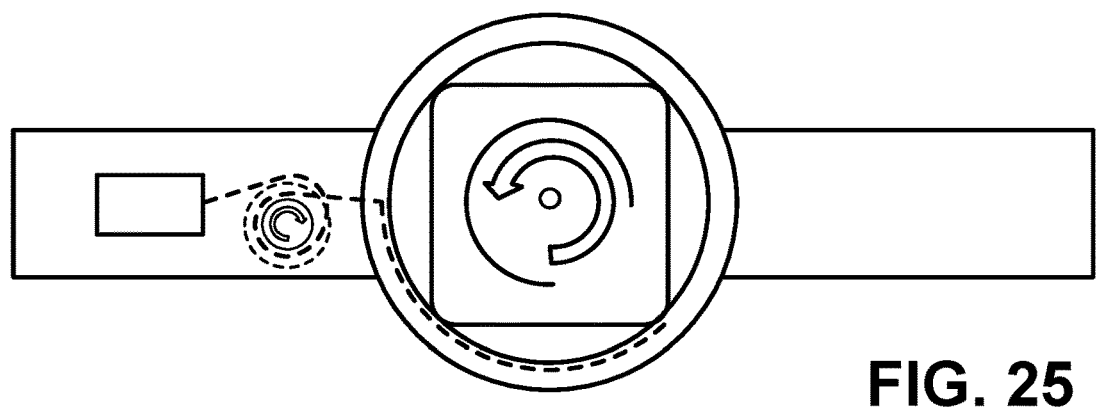
FIG. 25 is an example of a rotary mechanism that allows the antenna to be rotated by 270 degrees within the wearable antenna assembly.

FIG. 25 is an example of a rotary mechanism that allows the antenna to be rotated by 270 degrees within the wearable antenna assembly. Migration of the implant in the body can require repositioning of the WAA antenna within the belt to avoid polarization of transmission and encourage optimized transmission. The embedded antenna is set into a circular housing in the WAA. The antenna is secured to the belt with a centered ball joint that allows rotational movement along the arced track of the belt. The antenna has a matching pin that aligns to the groove of the track of the belt. The arced track for rotation allows rotation between from about 0° to about 270°. The ball joint is designed with resistance so that movement of the antenna within the house must be deliberate, requiring force to move the antenna along the track. The coaxial cable for the transmitting antenna is run through the circular track of the belt. Any slack cabling is wound on its own ball joint, as the antenna rotates. Once the antenna is set at the appropriate rotation for transmission the antenna and cabling can be re-concealed with a sleeve or cover.

Figure 26:
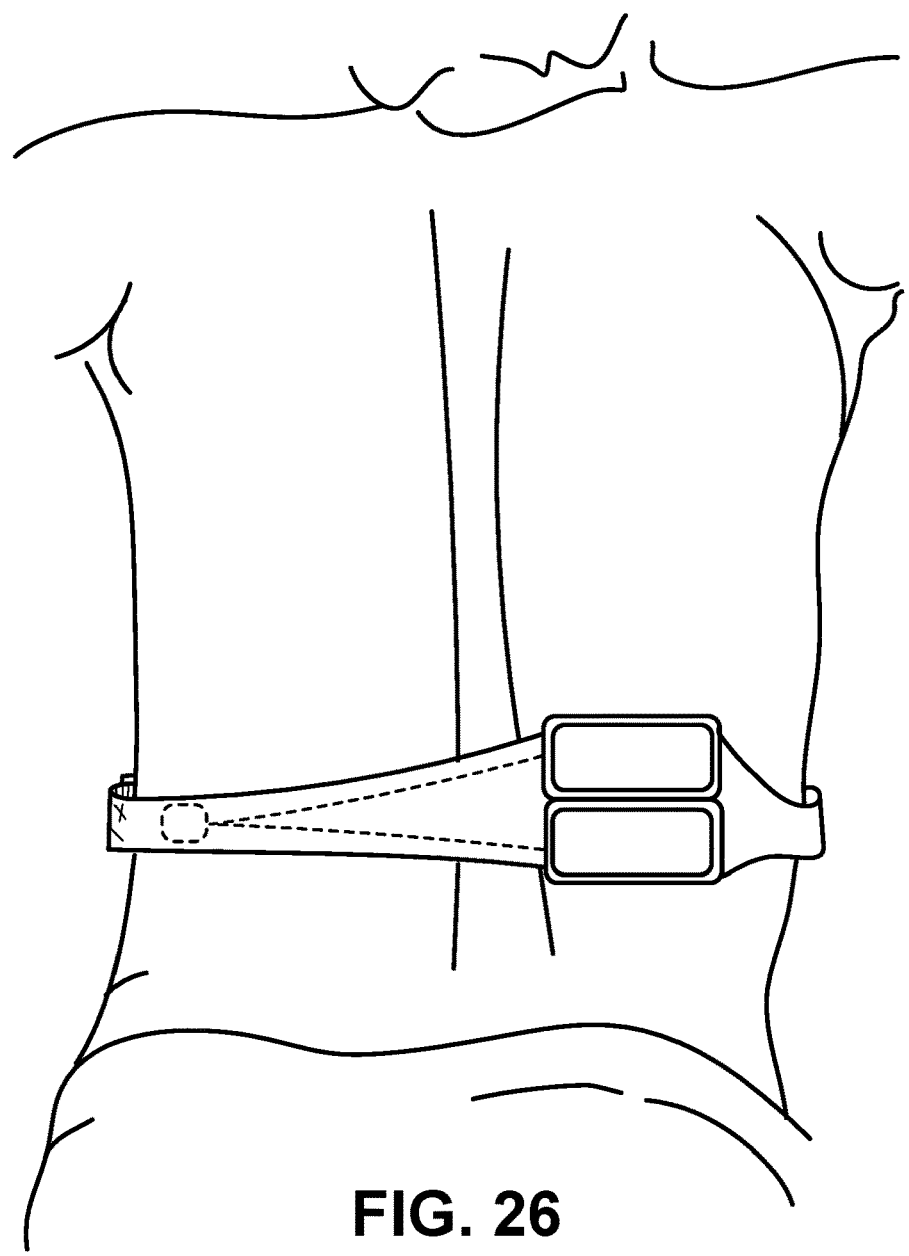
FIG. 26 demonstrates the use of two flexible transmitting antennas within the wearable antenna assembly to power multiple leads simultaneously with distinct parameters.

FIG. 26 demonstrates the use of two antennas to power two leads simultaneously with separate parameters and amplitudes in the wearable antenna assembly. The microwave field stimulator is able to program and transmit independent power parameters to the two implanted leads. This allows for control over two or more leads, implanted at different locations. The antennas are stacked and are able to be placed off center front the spine.

Figure 27:
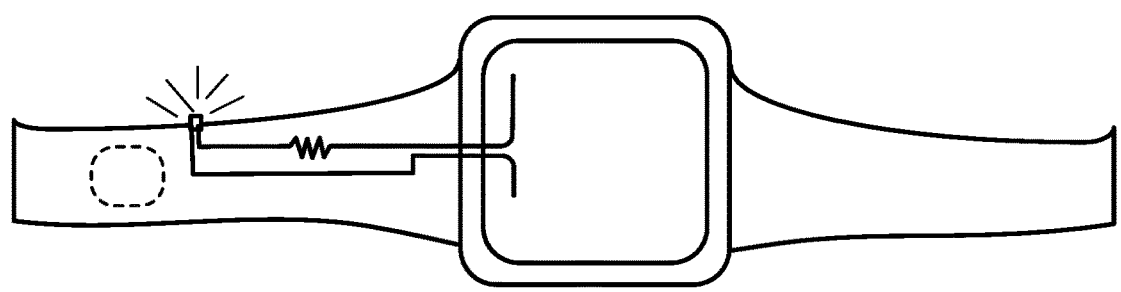
FIG. 27 is an example circuit that can be used to inform the user that RF energy is being transmitted.

FIG. 27 is an example circuit that can be used to inform the user that RF energy is being transmitted. An indicator light is build into the control panel of the belt. This indicator light illuminates when the belt is transmitting energy to the implant. This indicator light is independent from the "power on" indicator. If the microwave field stimulator is not able to transmit power to the transmitting antenna, the indicator light will not illuminate. This indicator light will remain illuminated as long as RF energy is transmitted out of the embedded antenna. This indicator light can be a small LED, OLED, LCD, or a signal sent to a smart phone application via Bluetooth. The indicator light works through a small dipole placed at the edge of the embedded antenna, which receives the energy to power the indicator light. A resistor is used to tune the current to the indicator light.

Figure 28:
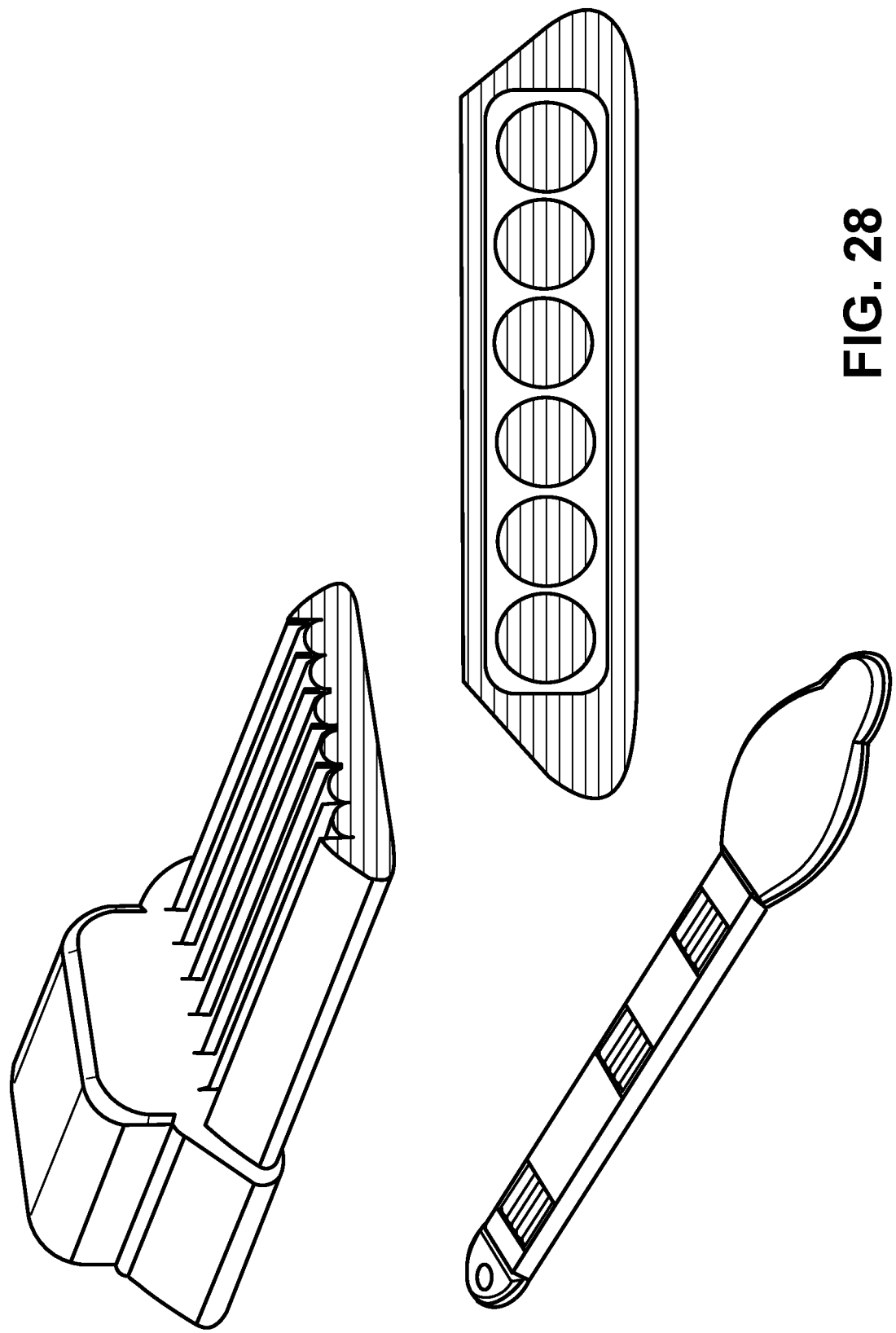
FIG. 28 illustrates the use of signal rails within the belt to allow placement of the battery, control panel, and microwave field stimulator in interchangeable locations along the wearable antenna assembly.

FIG. 28 illustrates the use of signal rails within the belt to allow placement of the battery, control panel, and microwave field stimulator in interchangeable locations along the wearable antenna assembly. In this embodiment of the WAA, the microwave field stimulator, battery, and control panel are "floating" modules on the belt. These modules are secured to the belt via tracks and conduct energy/signal through the rails. In certain embodiments, the tracks are keyed so as to prevent incorrect orientation of the modules connecting to the wrong rails. The modules complete their circuitry once attached to the belt set into the tracks. The modules are then secured on the belt. The user is able to move the modules independent of each other allowing the user to place the modules on comfortable places on the belt. The various body sizes and shapes require the modules to be adjustable. The rails can be set for specific signals including but not limited to: battery-power, ground, button-switches, RF Signal, light indicator.

FIG. 29 is an example of the placement of the microwave field stimulator near the antenna on the wearable antenna assembly. The microwave field stimulator is positioned close to the transmitting antenna on the belt to reduce transmission loss from the cable. This allows for a shorter, lower-profile cable. The microwave field stimulator can be located on either side of the antenna. In certain embodiments, the microwave field stimulator may be located on the backside of the antenna.

FIG. 30 illustrates the use of differential positioning sensors placed on the wearable antenna to alert the user and adjust stimulation. The belt is affixed with positioning sensors that will alert the user if the belt shifts to a position on the body that could produce less than optimal transmission of RF energy to the implanted lead. The dorsal sensors can be placed on the belt close to the transmitting antenna. The ventral sensors can be placed at the belt clip or at the 180° mark from the antenna. The microwave field stimulator calculates the differential position between the ventral and dorsal aspects of the WAA and can alert the user when the WAA has shifted enough that transmission may be interrupted. The microwave field stimulator can calculate the differential position between the ventral dorsal aspects of the WAA and automatically adjust the amplitude when the user has changed positions that are known to need corrective actions. The indication to the user can be vibration from the microwave field stimulator. Until the user has corrected the placement, the microwave field stimulator can vibrate or alert the user through a smartphone app via Bluetooth.

Figure 31:
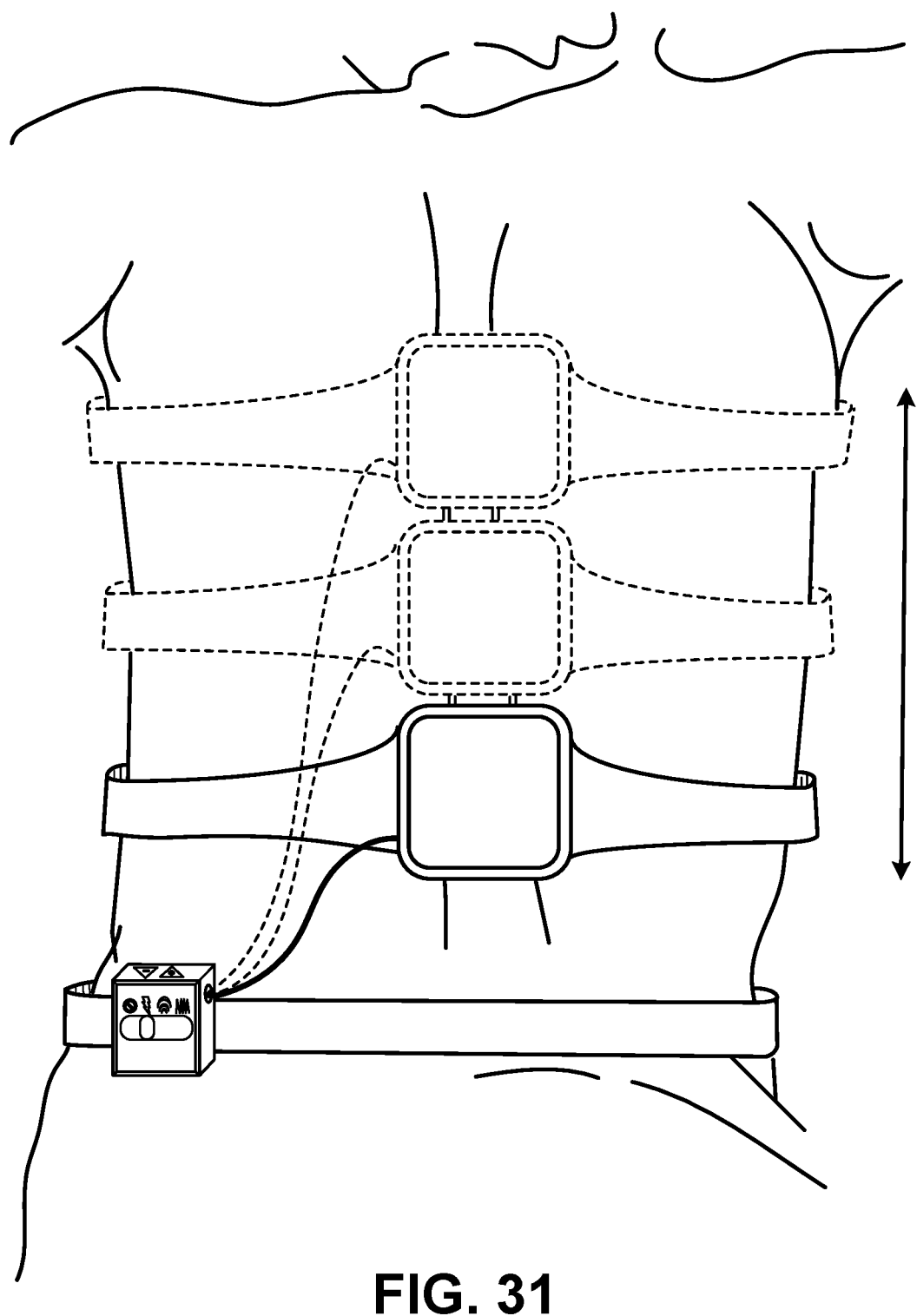
FIGS. 31 and 32 show an example of a belt fastening system with sensor contacts to activate/deactivate the generation of the signal.
Figure 32:
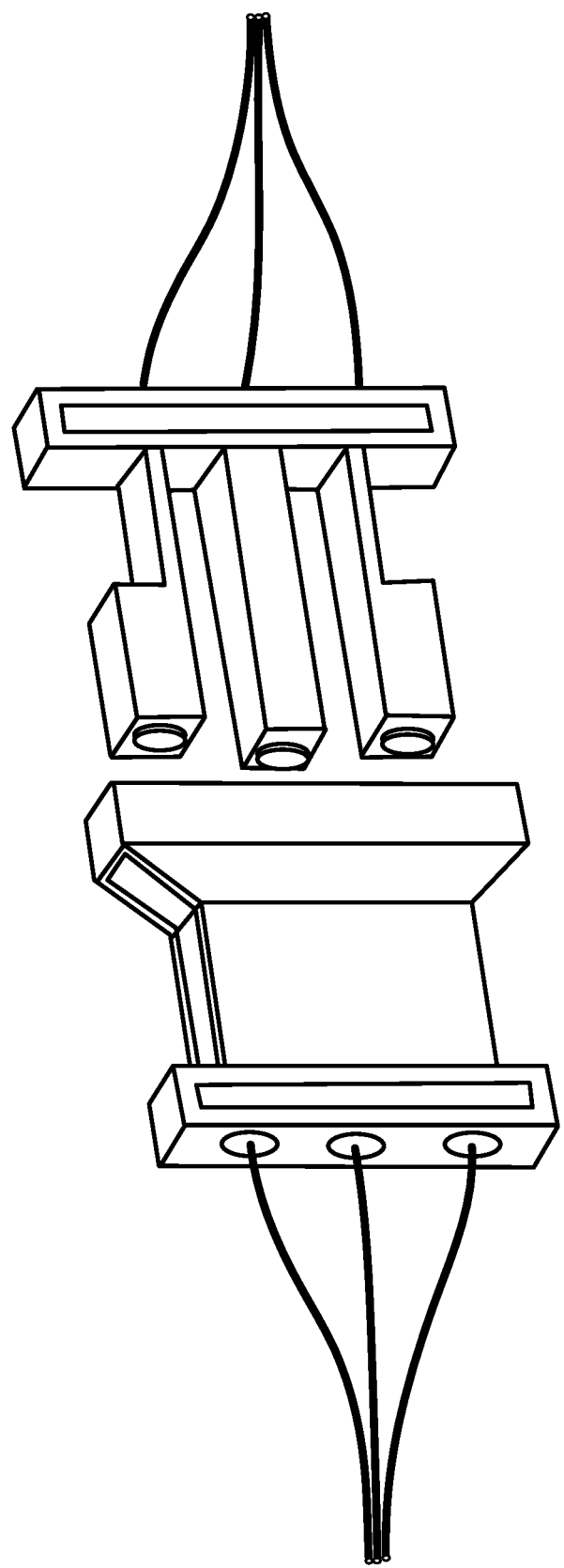

FIGS. 31 and 32 show an example of a belt fastening system with sensor contacts to activate/deactivate wireless stimulating electronics. The fastener contains male electrical contacts on the female side of the parachute clip and female electrical contacts on the male side of the parachute clip. The contacts can be connected to the circuitry of the battery. When the parachute clips are engaged, the circuit is closed, allowing the battery to power the microwave field stimulator. Once the belt is unfastened, the circuit is open, disabling the power from the battery to the microwave field stimulator. In other embodiments the electrical contacts can be used as a smart sensor to notify the electronics that the user is going to take off or adjust the belt. The microwave field stimulator could then slowly power down the amplitude of stimulation to avoid uncomfortable VSWR interactions with the antenna and the patient.

Figure 33:
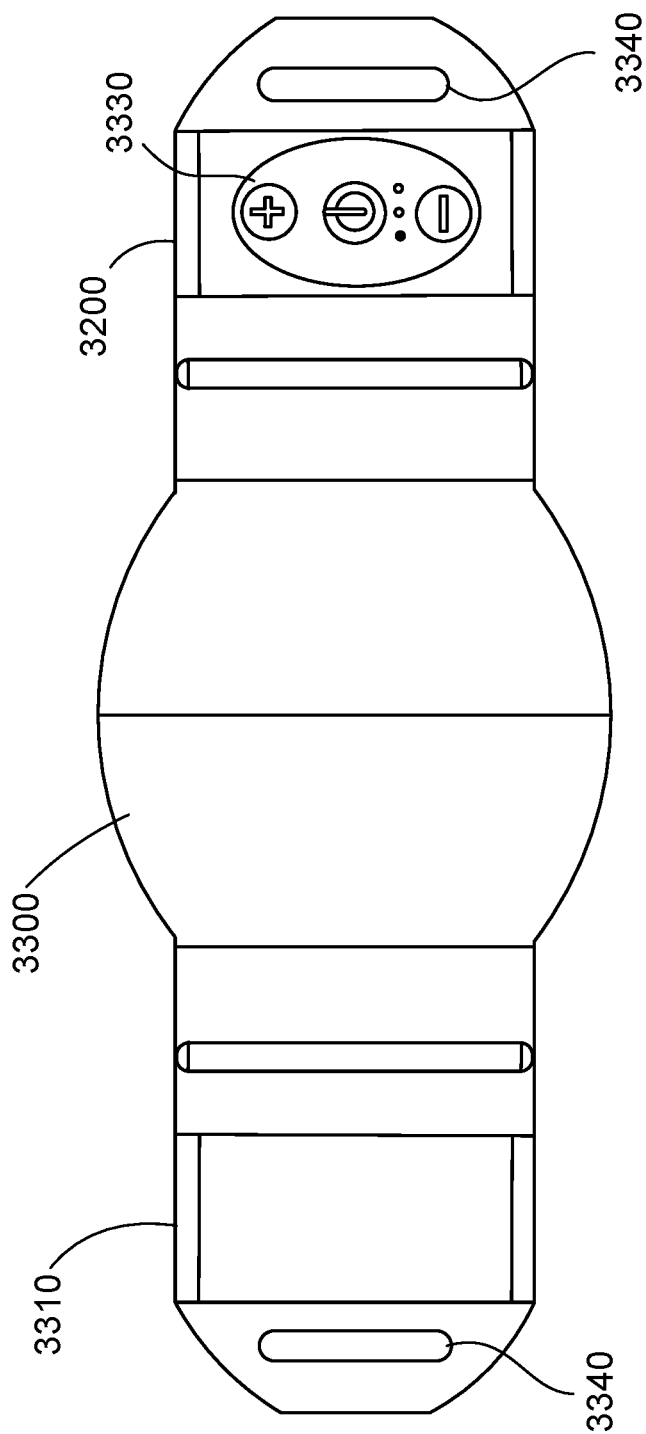
FIG. 33 shows a top view of a wearable antenna assembly according to some embodiments of the present invention.

FIG. 33 shows a top view of a wearable antenna assembly according to some embodiments of the present invention. As shown, a center portion 3300 is disposed toward the longitudinal middle of the wearable antenna assembly. Left portion 3310 and right portion 3320 are disposed at either longitudinal side of center portion 3300. As control panel 3330 is provided on the top face of right portion 3320. Fastening members 3340 are provided to allow fastening of an elastic belt or otherwise to the portion of the wearable antenna assembly shown. As such, the portion of the wearable antenna assembly as shown in FIG. 33 may be less than the full length of a full wearable antenna assembly. For example, the portion of wearable antenna assembly shown in FIG. 33 may be approximately 30 centimeters long. An elastic ban attached at each end to fastening members 3340 can then be provided to make the full length or circumference of the entire wearable antenna assembly the length desired. In some instances, an elastic band will be provided so that the entire wearable antenna assembly circumference including the elastic band and the portion shown in FIG. 33 will be wearable around the torso of a patient, as previously discussed. Nonetheless, other configurations are possible, such as using a different attachment to fastening members 3340, different forms of fastening members than those shown in FIG. 33, different lengths of attachments to fastening members 3340, and a different length for the portion shown in FIG. 33.

Figure 34:
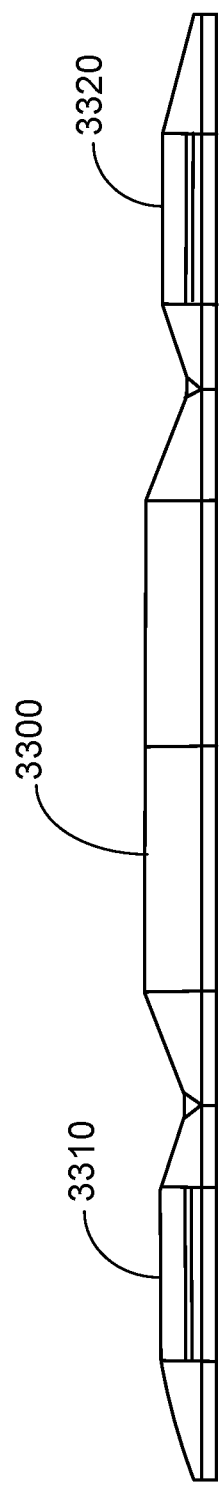
FIG. 34 shows a side view of a wearable antenna assembly according to some embodiments of the present invention.

FIG. 34 shows a side view of a wearable antenna assembly according to some embodiments of the present invention. As shown, center portion 3300 is disposed longitudinally between left portion 3310 and right portion 3320. As further shown, narrower portions between center portion 3300 and left portion 3310 and between center portion 3300 and right portion 3320 may be provided to allow the wearable antenna assembly to flex and contour to the patients body. These portions may also or alternatively be provided as a flexible material, such as foam, rubber, or otherwise.

Figure 35A:
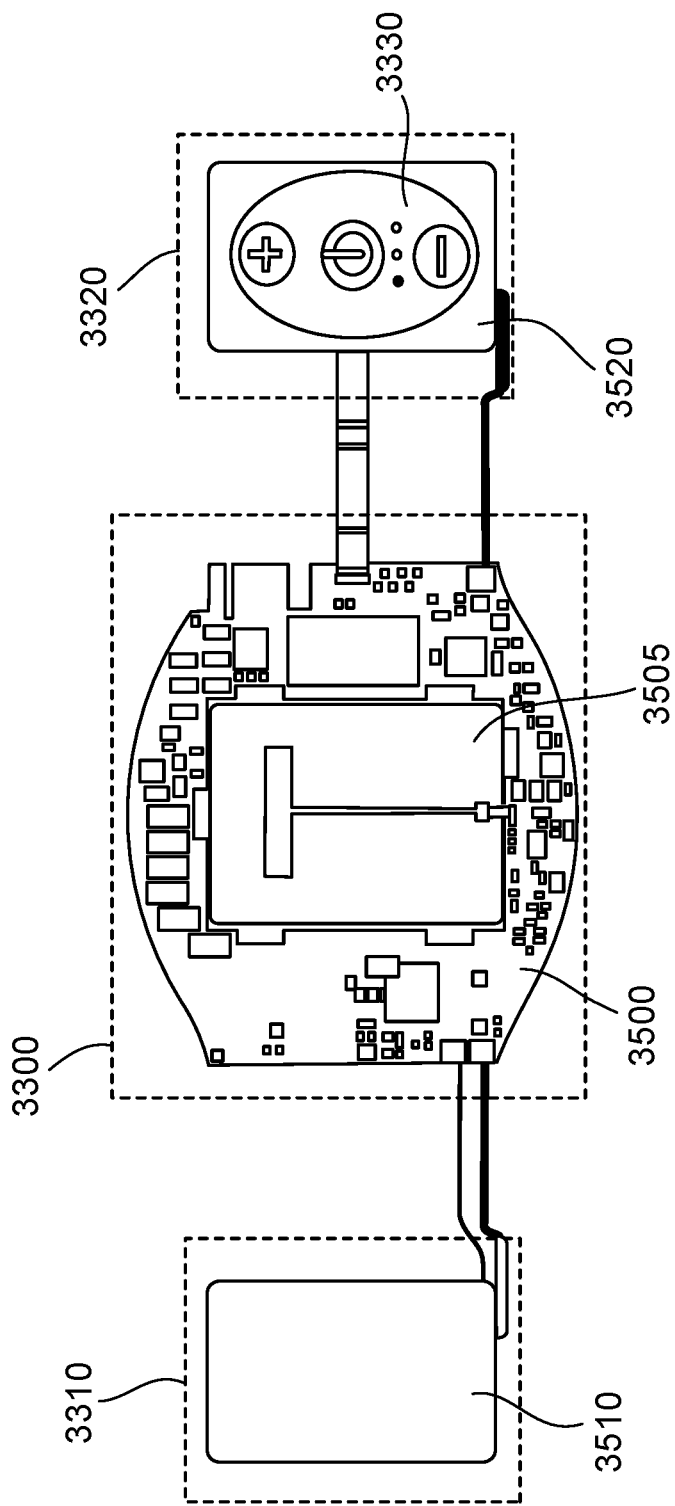
FIG. 35A shows a top view of a wearable antenna assembly with certain outer portions removed according to some embodiments of the present invention.

FIG. 35A shows a top view of a wearable antenna assembly with certain outer portions removed according to some embodiments of the present invention. As shown, center portion 3300 contains a MFS 3500 and a transmitting antenna 3505. Transmitting antenna 3505 may be a patch antenna provided in the center of center portion 3300. MFS 3500 may be a provided as a printed circuit board with various circuitry provided thereon. As shown, MFS 3500 may be provided as disposed essentially surrounding transmitting antenna 3505. Left portion 3310 contains left battery 3510. Right portion 3320 contains control panel 3310 as well as right battery 3520 provided below control panel 3310.

Figure 35B:
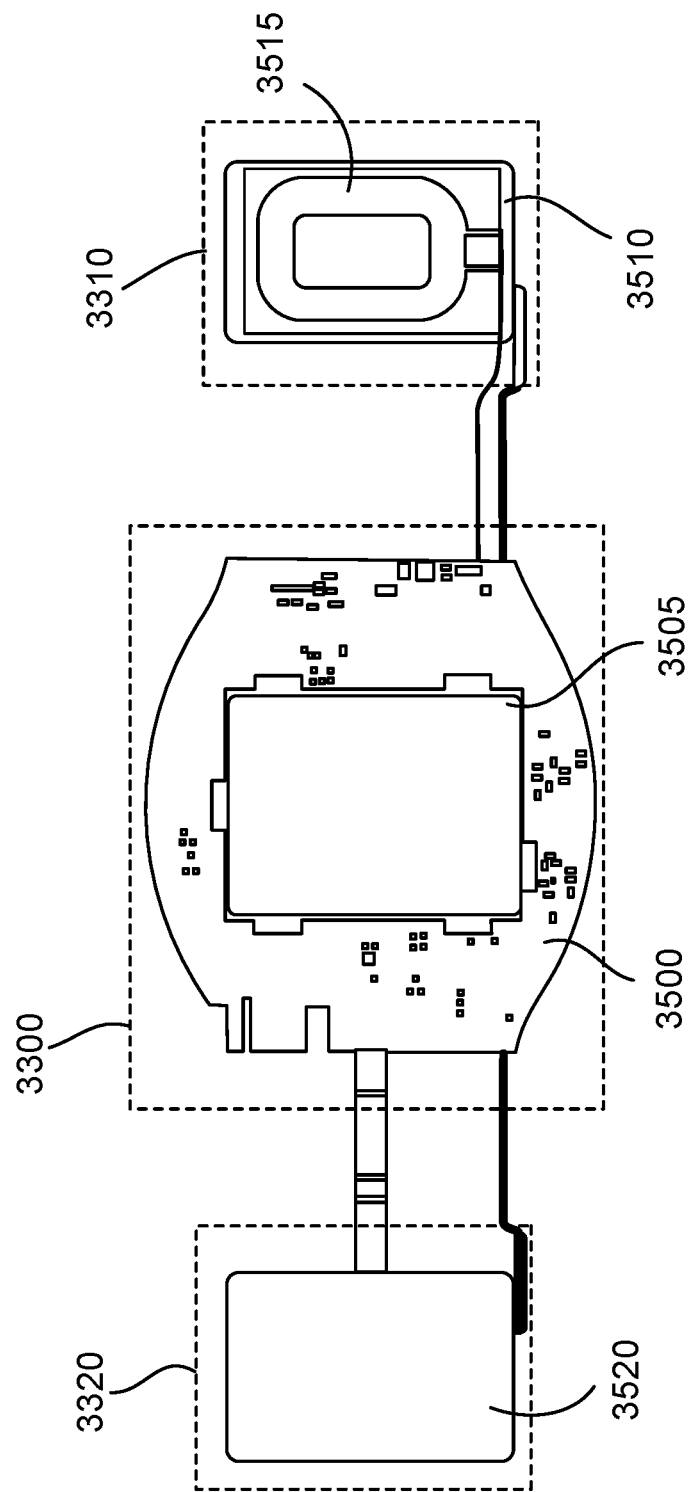
FIG. 35B shows a bottom view of a wearable antenna assembly with certain outer portions removed according to some embodiments of the present invention.

FIG. 35B shows a bottom view of a wearable antenna assembly with certain outer portions removed according to some embodiments of the present invention. As shown, center portion 3300 contains MFS 3500 and transmitting antenna 3505. Left portion 3310 contains wireless charging coil 3515 as well as left battery 3510 provided below wireless charging coil 3515. Right portion 3320 contains right battery 3520.

Figure 36C:
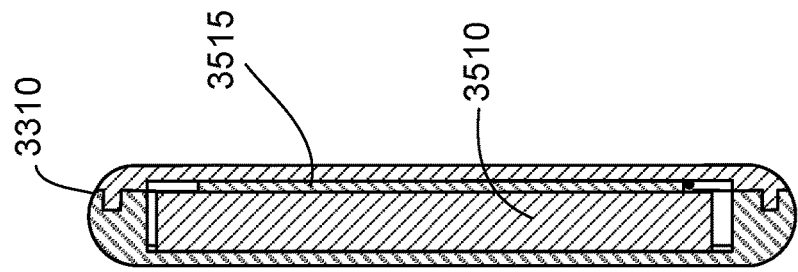
FIGS. 36A, 36B, and 36C show cross section cutaway views of portions of a wearable antenna assembly according to some embodiments of the present invention.
Figure 36B:
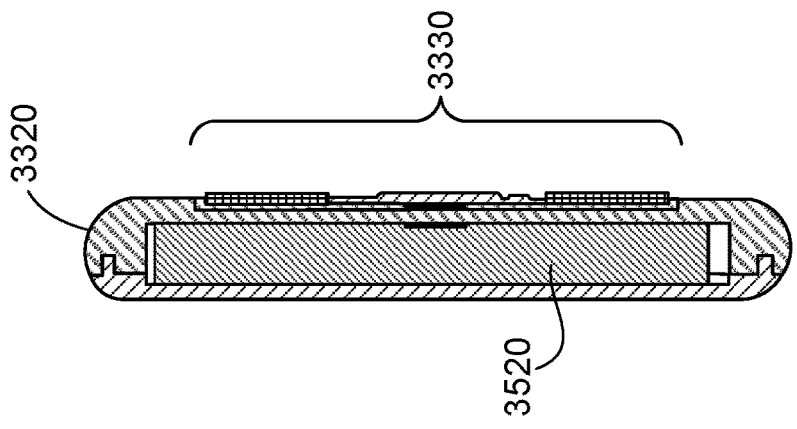
Figure 36A:
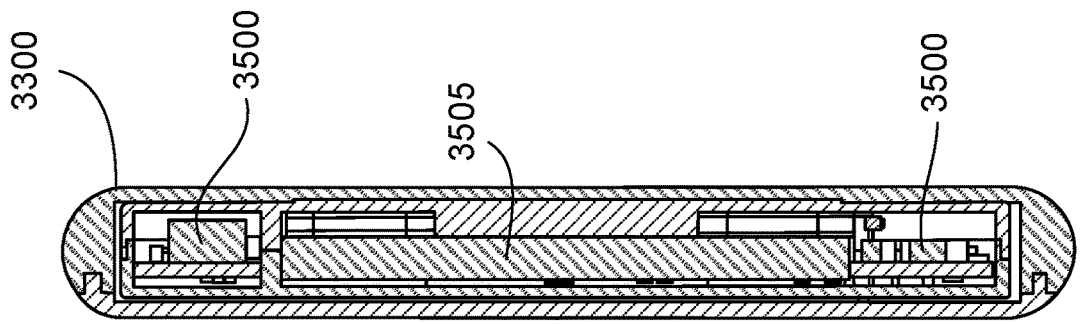

FIGS. 36A, 36B, and 36C show cross section cutaway views of portions of a wearable antenna assembly according to some embodiments of the present invention. FIG. 36A shows a cross section cutaway view of center portion 3300. As shown, transmitting antenna 3505 is disposed in the middle of center portion 3300. MFS 3500 is disposed in the area surrounding transmitting antenna 3505. FIG. 36B shows a cross section cutaway view of right portion 3320. As shown, right battery 3520 is provided therein, and control panel 3330 is provided on the top face of right portion 3320. FIG. 36C shows a cross section cutaway view of left portion 3310. As shown, left battery 3510 and wireless charging coil 3515 are provided therein.

Figure 37:
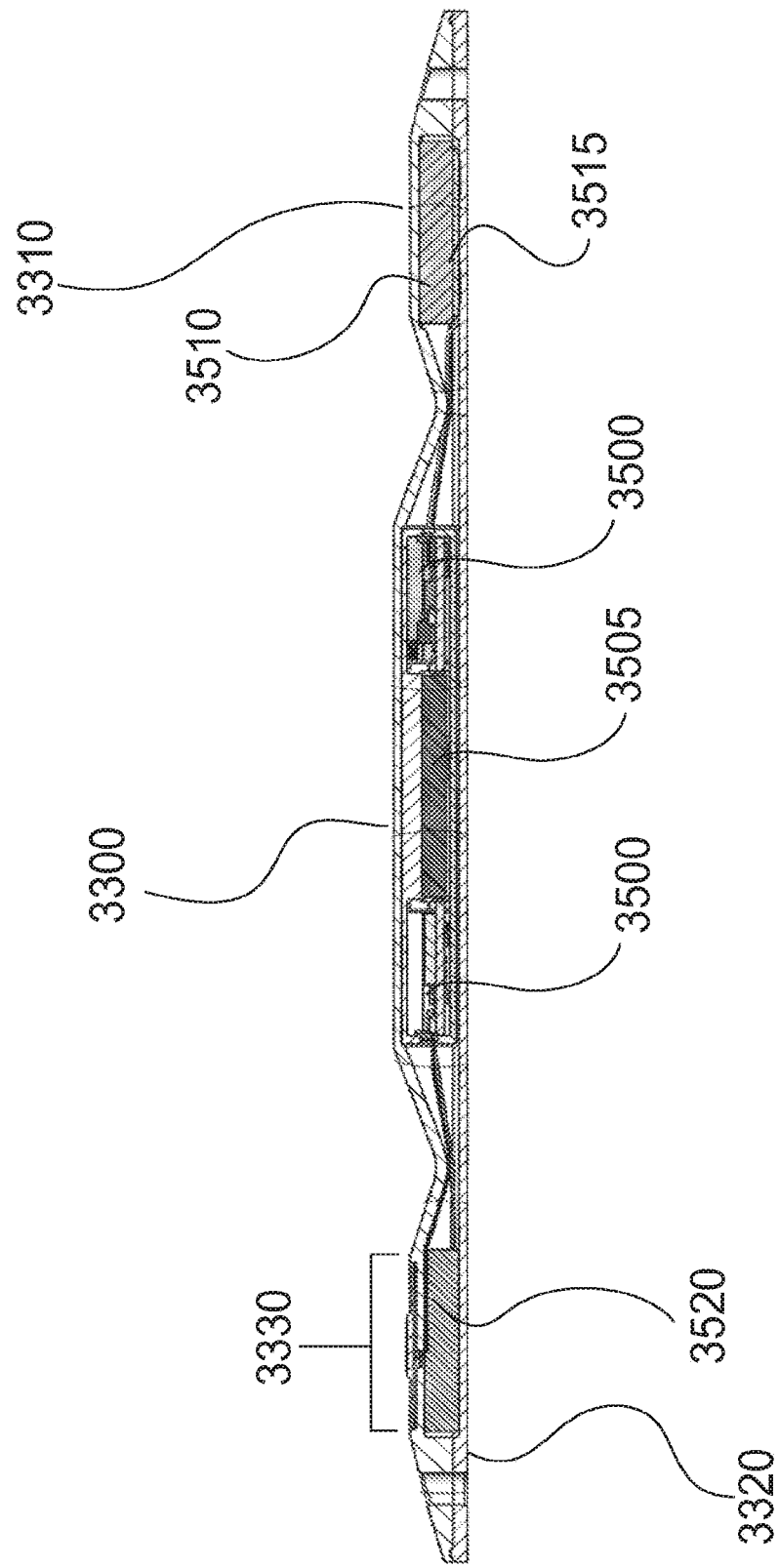
FIG. 37 shows a longitudinal cutaway view of a wearable antenna assembly according to some embodiments of the present invention.

FIG. 37 shows a longitudinal cutaway view of a wearable antenna assembly according to some embodiments of the present invention. As shown, transmitting antenna 3505 and MFS 3500 are provided in center portion 3300. As shown, right battery 3520 and control panel 3330 are provided in right portion 3320. As shown, left battery 3510 and wireless charging coil 3515 are provided therein are provided in left portion 3310.

Figure 38:
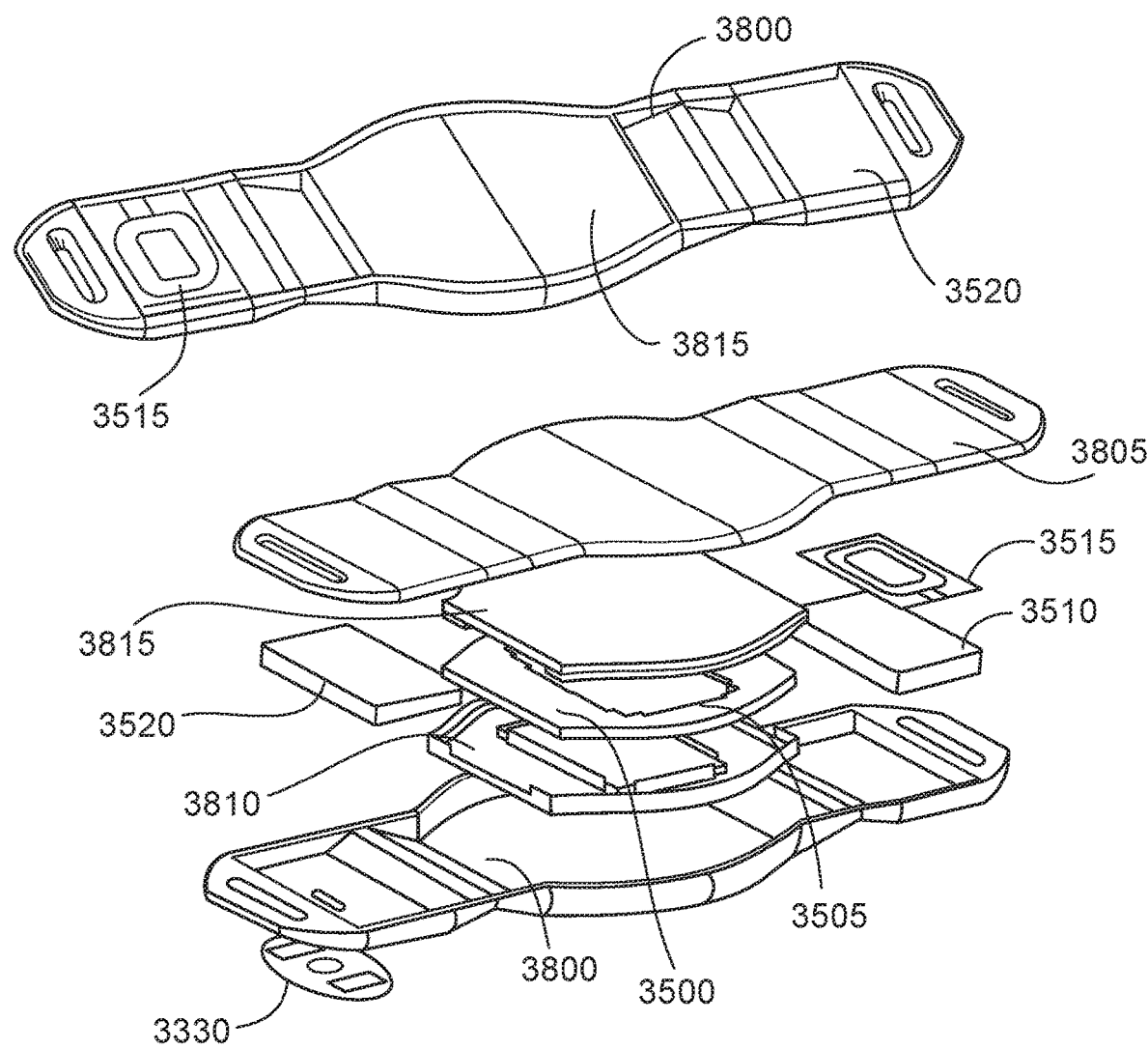
FIG. 38 shows an exploded 3D view of a wearable antenna assembly according to some embodiments of the present invention.

FIG. 38 shows an exploded 3D view of a wearable antenna assembly according to some embodiments of the present invention. As shown, center portion 3300, which contains MFS 3500 and transmitting antenna 3505, may contain a top rigid cover 3810 and a bottom rigid cover 3815. In such a configuration, top rigid cover 3810 and bottom rigid cover 3815 close around MFS 3500 and transmitting antenna 3505 to form a rigid, protective shell around those components. This is advantageous as the circuitry of MFS 3500 and the thin surface of transmitting antenna 3505 may be fragile or prone to damage if bent. This rigid shell along with the other components previously discussed may then be enclosed in top skin 3800 and bottom skin 3805. Top skin 3800 and bottom skin 3805 may serve to maintain all of the various functional components contained an in place in the wearable antenna assembly. Furthermore, top skin 3800 and bottom skin 3805 may be provided as a flexible material. With such a configuration, the wearable antenna assembly shown in this figure may be sufficiently flexible to contour to the patient's body despite the rigid components contained therein. As such, the flexible material of top skin 3800 and bottom skin 3805 may allow the wearable antenna assembly as shown in this figure to be worn as a belt despite it containing various rigid components.

The construction and arrangement of the elements as shown in the exemplary embodiments are illustrative only. Although only a few embodiments of the present disclosure have been described in detail, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements. The elements and assemblies may be constructed from any of a wide variety of materials that provide sufficient strength or durability, in any of a wide variety of colors, textures, and combinations. Additionally, in the subject description, the word "exemplary" is used to mean serving as an example, instance, or illustration. Any embodiment or design described herein as "exemplary" is not necessarily to be construed as preferred or advantageous over other embodiments or designs. Rather, use of the word "exemplary" is intended to present concepts in a concrete manner. Accordingly, all such modifications are intended to be included within the scope of the present disclosure. Other substitutions, modifications, changes, and omissions may be made in the design, operating conditions, and arrangement of the preferred and other exemplary embodiments without departing from the scope of the appended claims.

What is claimed is:

1. A wearable antenna assembly, comprising:
   an antenna configured to send one or more stimulus signals carrying electrical energy to a wireless tissue stimulator when the wireless tissue stimulator is implanted within a body, wherein the antenna comprises a dielectric layer that directly contacts the body and a non-conductive layer between a conductor layer of the antenna and the dielectric layer; and
   a housing carrying the antenna, the housing comprising a first attachment feature configured to engage a second attachment feature on a wearable article for positioning the antenna adjacent the body when the wearable article is worn on the body.

2. The wearable antenna assembly of claim 1, wherein the wearable article comprises an adjustable strap.

3. The wearable antenna assembly of claim 2, wherein the first attachment feature comprises an open slot, and wherein the second attachment feature comprises a connector tab.

4. The wearable antenna assembly of claim 1, further comprising the wearable article.

5. The wearable antenna assembly of claim 1, wherein the housing comprises a belt member.

6. The wearable antenna assembly of claim 1, wherein the antenna comprises a plurality of layers arranged such that when the wearable antenna assembly is worn, the plurality of layers is oriented substantially parallel to a skin surface of the body, wherein the plurality of layers comprise the dielectric layer.

7. The wearable antenna assembly of claim 6, wherein the plurality of layers comprises:
   a ground plane located distal to the body;
   the conductor layer located between the ground plane and the skin surface of the body;
   a second non-conductive layer located between the ground plane and the conductor layer; and
   wherein the dielectric layer is located between the conductor layer and the skin surface of the body.

8. The wearable antenna assembly of claim 1, wherein the dielectric layer that directly contacts the body is in contact with a skin surface of the body when the wearable antenna assembly is worn on the body.

9. The wearable antenna assembly of claim 1, wherein the antenna is tuned with the dielectric layer to sufficiently match a coupling of a skin surface of the body to facilitate transmission of the one or more stimulus signals into the body.

10. The wearable antenna assembly of claim 1, wherein the antenna comprises a patch antenna.

11. The wearable antenna assembly of claim 1, further comprising:
    a control circuit configured to provide one or more input signals to the antenna; and
    a battery that provides electrical power to the control circuit.

12. The wearable antenna assembly of claim 11, wherein the battery is rechargeable.

13. The wearable antenna assembly of claim 11, wherein the battery is removable from the housing.

14. The wearable antenna assembly of claim 11, wherein the control circuit comprises a microwave field stimulator.

15. The wearable antenna assembly of claim 11, further comprising a control panel with at least one user interface button.

16. The wearable antenna assembly of claim 15, wherein the control panel comprises a first user interface button that controls at least one neurostimulation setting of control circuitry.

17. The wearable antenna assembly of claim 16, wherein the at least one neurostimulation setting comprises a setting for one or more of an amplitude, a pulse width, a frequency, and a preset program.

18. The wearable antenna assembly of claim 16, wherein the control panel comprises a second user interface button that controls a setting of the first user interface button.

19. A wearable antenna assembly, comprising:
    an antenna configured to send one or more stimulus signals carrying electrical energy to a wireless tissue stimulator when the wireless tissue stimulator is implanted within a body, wherein the antenna comprises a dielectric layer that directly contacts the body and a non-conductive layer between a conductor layer of the antenna and the dielectric layer, wherein the one or more stimulus signals comprise one or more first stimulus signals, and wherein the wearable antenna assembly further comprises an additional antenna configured to send one or more second stimulus signals carrying additional electrical energy to an additional wireless tissue stimulator when the additional wireless tissue stimulator is implanted within the body; and
    a housing carrying the antenna, the housing comprising a first attachment feature configured to engage a second attachment feature on a wearable article for positioning the antenna adjacent the body when the wearable article is worn on the body.

20. The wearable antenna assembly of claim 19, wherein the one or more second stimulus signals are distinct from the one or more first stimulus signals.

* * * * *